(12) United States Patent
Terada et al.

(10) Patent No.: US 10,813,634 B2
(45) Date of Patent: Oct. 27, 2020

(54) KNOT FORMING DEVICE FORMING KNOT BY TRANSFERRING END OF TYING MEDIUM THROUGH MECHANICAL OPERATIONS

(71) Applicant: Brother Kogyo Kabushiki Kaisha, Nagoya (JP)

(72) Inventors: Kohei Terada, Kiyosu (JP); Daisuke Ishii, Nagoya (JP); Naohisa Kinoshita, Nagoya (JP); Masato Kobayashi, Yokohama (JP)

(73) Assignee: Brother Kogyo Kabushiki Kaisha, Nagoya (JP)

( * ) Notice: Subject to any disclaimer, the term of this patent is extended or adjusted under 35 U.S.C. 154(b) by 354 days.

(21) Appl. No.: 15/719,631

(22) Filed: Sep. 29, 2017

(65) Prior Publication Data

US 2018/0036000 A1 Feb. 8, 2018

Related U.S. Application Data

(63) Continuation-in-part of application No. PCT/JP2016/058482, filed on Mar. 17, 2016, and a
(Continued)

(30) Foreign Application Priority Data

Mar. 31, 2015 (JP) .................. 2015-074486
Mar. 31, 2015 (JP) .................. 2015-074487
Mar. 31, 2015 (JP) .................. 2015-074488

(51) Int. Cl.
*A61B 17/04* (2006.01)
*A61B 17/062* (2006.01)
*A61B 17/00* (2006.01)

(52) U.S. Cl.
CPC ...... *A61B 17/0469* (2013.01); *A61B 17/0483* (2013.01); *A61B 17/0491* (2013.01);
(Continued)

(58) Field of Classification Search
CPC ............ A61B 17/0483; A61B 17/0491; A61B 17/062; A61B 17/0625; A61B 2017/0472;
(Continued)

(56) References Cited

U.S. PATENT DOCUMENTS 5,207,694 A 5/1993 Broomé
5,336,230 A * 8/1994 Leichtling .......... A61B 17/0469
128/898

(Continued)

FOREIGN PATENT DOCUMENTS

JP H08-252257 A1 10/1996

OTHER PUBLICATIONS

International Search Report and Written Opinion (Application No. PCT/JP2016/058482) dated May 31, 2016 (with English translation).
(Continued)

*Primary Examiner* — Katherine M Shi
*Assistant Examiner* — Lindsey Bachman
(74) *Attorney, Agent, or Firm* — Burr & Brown, PLLC

(57) ABSTRACT

First and second arms have first and second retaining members, respectively. A switching mechanism switches a retained state of a first position of a tying medium between first and second states. In the first and second states, the first position is retained by the first and second retaining members at first and second retaining positions, respectively. A loop retaining member retains a loop around the second arm in a path extending from the first retaining position through second and third positions to a fourth position of the tying medium. The second position intersects the third position as
(Continued)

a result of the loop such that the third position is closer to the first retaining position than the second position in the path. A moving portion moves the loop relative to the second arm to change a relative positional relationship between the loop and the first position on the path.

34 Claims, 30 Drawing Sheets

Related U.S. Application Data continuation-in-part of application No. PCT/JP2016/058484, filed on Mar. 17, 2016, and a continuation-in-part of application No. PCT/JP2016/058483, filed on Mar. 17, 2016.

(52) U.S. Cl.
CPC ........ *A61B 17/062* (2013.01); *A61B 17/0625* (2013.01); *A61B 2017/00353* (2013.01); *A61B 2017/0474* (2013.01)

(58) Field of Classification Search
CPC .... A61B 2017/0474; A61B 2017/0475; A61B 2017/0477; A61B 2017/0482; A61B 2017/0485; A61B 2017/0609
See application file for complete search history.

(56) References Cited

U.S. PATENT DOCUMENTS

| | | |
|---|---|---|
| 5,417,700 A | 5/1995 | Egan |
| 5,480,406 A | 1/1996 | Nolan et al. |
| 5,797,928 A * | 8/1998 | Kogasaka .......... A61B 17/0469 606/139 |
| 5,814,069 A | 9/1998 | Schulze et al. |
| 7,416,556 B2 | 8/2008 | Jackson |

OTHER PUBLICATIONS

International Search Report and Written Opinion (Application No. PCT/JP2016/058483) dated May 31, 2016 (with English translation).
International Search Report and Written Opinion (Application No. PCT/JP2016/058484) dated May 31, 2016 (with English translation).
English Translation of International Preliminary Report on Patentability for PCT/JP2016/058482, dated Oct. 12, 2017 (12 pages).
English Translation of International Preliminary Report on Patentability for PCT/JP2016/058483, dated Oct. 12, 2017 (12 pages).
English Translation of International Preliminary Report on Patentability for PCT/JP2016/058484, dated Oct. 12, 2017 (12 pages).

\* cited by examiner

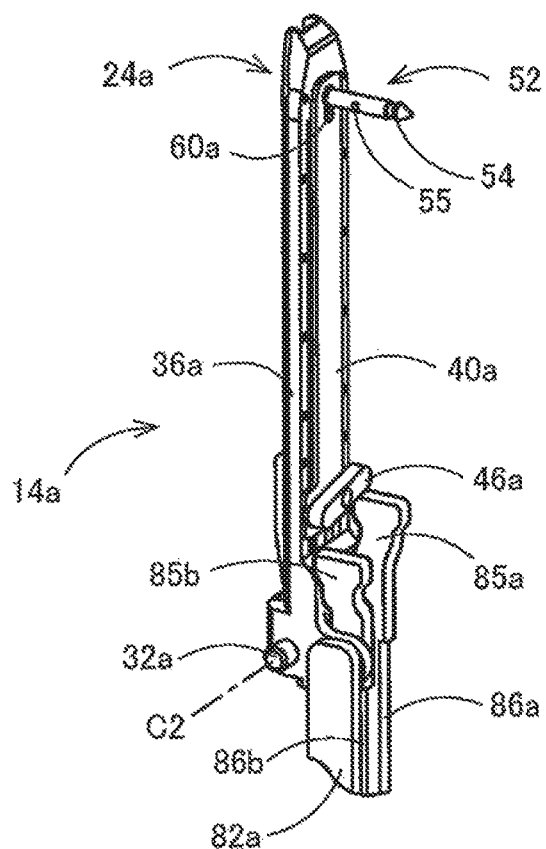
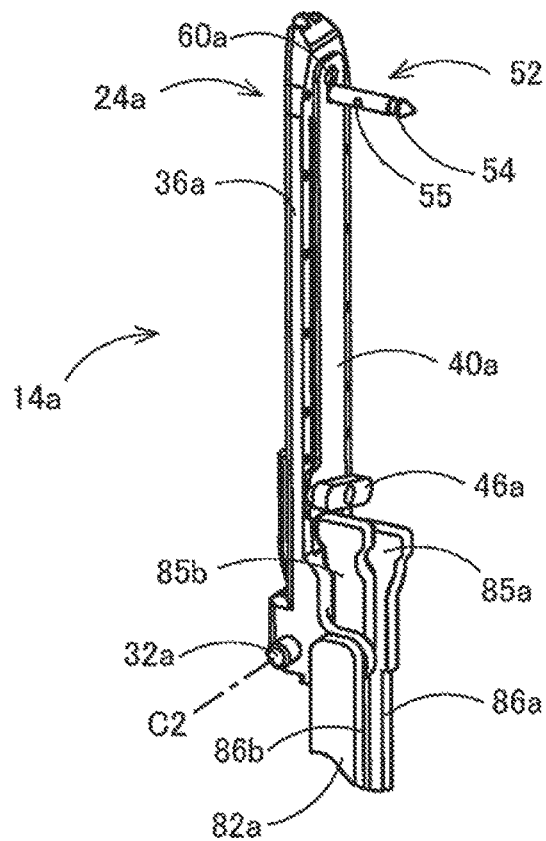

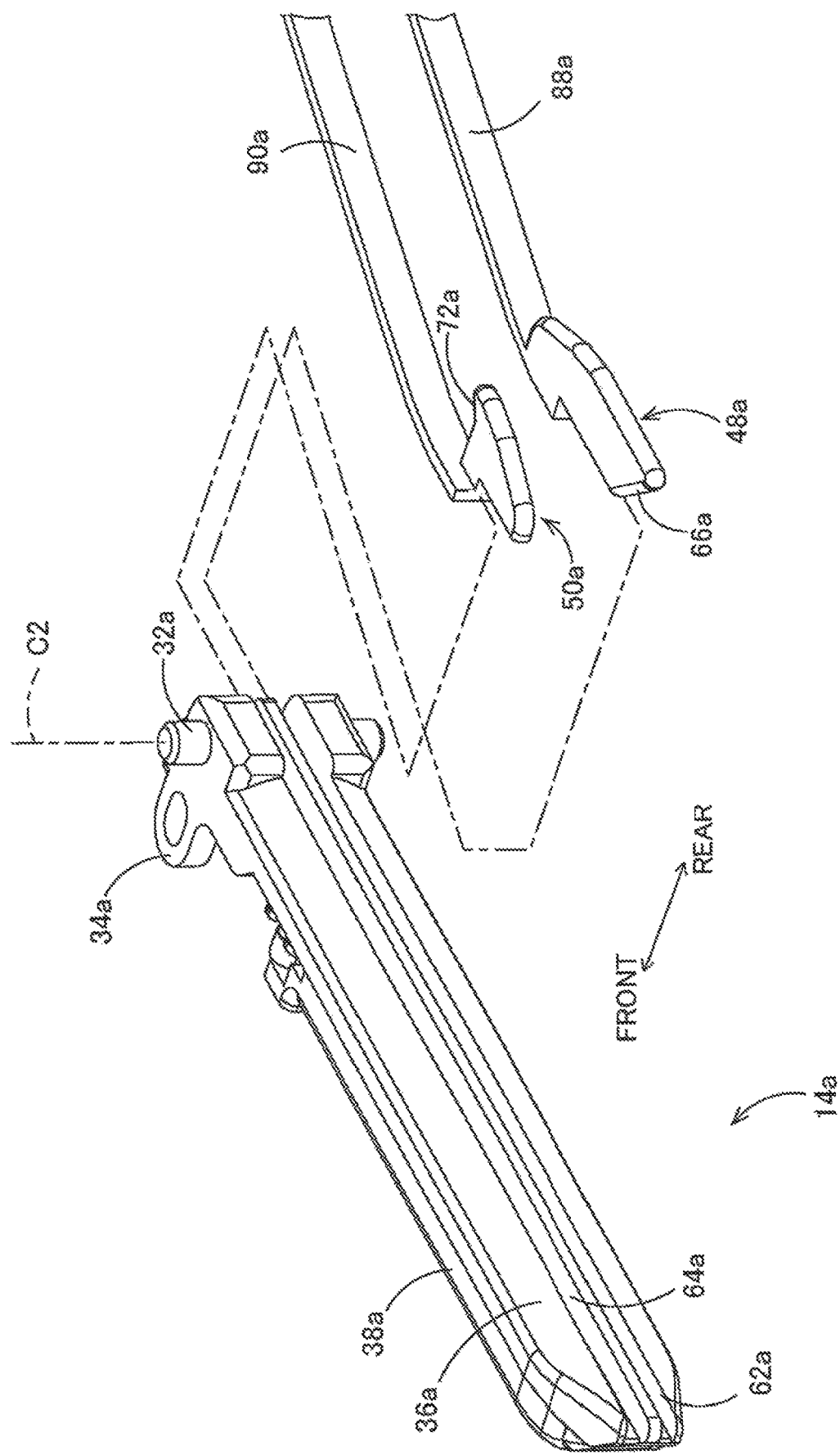

KNOT FORMING DEVICE FORMING KNOT BY TRANSFERRING END OF TYING MEDIUM THROUGH MECHANICAL OPERATIONS

CROSS REFERENCE TO RELATED APPLICATION

This application is a by-pass continuation-in-part application of International Application No. PCT/JP2016/058482 filed Mar. 17, 2016 in the Japan Patent Office acting as Receiving Office and claiming priority from Japanese Patent Application No. 2015-074486 filed Mar. 31, 2015, International Application No. PCT/JP2016/058483 filed Mar. 17, 2016 in the Japan Patent Office acting as Receiving Office and claiming priority from Japanese Patent Application No. 2015-074487 filed Mar. 31, 2015, and International Application No. PCT/JP2016/058484 filed Mar. 17, 2016 in the Japan Patent Office acting as Receiving Office and claiming priority front Japanese Patent Application No. 2015-074488 filed Mar. 31, 2015. The entire content of each of these applications are incorporated herein by reference.

TECHNICAL FIELD

The present disclosure relates to a knot forming device of a type that forms knots by transferring the end of the tying medium, such as a thread-like member.

BACKGROUND

Technologies have been proposed for forming a loop in and securing a tying medium, such as a thread-like member, including a technology that uses a suture anchor configured of metal or synthetic resin to clamp thread-like members together (U.S. Pat. No. 7,416,556, for example), and a technology for interlocking uneven formations pre-formed in the thread-like member itself (U.S. Pat. No. 5,207,694). A technology has also been proposed for welding thread-like members together using heat or ultrasound (U.S. Pat. No. 5,417,700, for example). However, thread-like members that are fixed by clamping together, interlocking, or welding the thread-like members have less binding strength and tightening ability than thread-like members that are tied with a knot.

Accordingly, various tying methods for forming, knots to secure a thread-like member by tying the thread-like member itself are well known, and various auxiliary tools for assisting in knot formation have been proposed (U.S. Pat. Nos. 5,336,230 and 5,480,406, for example).

For example, one technology describes forming knots through an operation similar to a manual operation in which two grasping devices are simply manipulated to control their positional relationship. This technology essentially requires that both grasping devices be operated. Another device disclosed in the art is an auxiliary suture tool for forming knots by performing a prescribed procedure. This technology requires that another grasper be used for transferring the thread-like member, since a knot cannot be formed with the auxiliary suture tool alone.

SUMMARY

While various devices for tying thread-like members have been proposed, none of these devices is more than an auxiliary tool for aiding the operator in tying the thread-like member and none successfully realizes a device for forming knots easily and reliably through mechanical operations.

With all of the above conventional devices, a human operator must determine which side of what thread-like member to pass the grasper, when and where to grasp the thread-like member, how many times and in what direction to wrap the thread-like member, and the like and must perform such operations based solely on information the operator takes in visually and the like. Accordingly, the operator must have had sufficient training in advance and must have proficient technique in practice in order to form knots using these tools. In other words, all of these tools require skill and cannot be defined as devices that can form knots reliably through simple mechanical operations.

In view of the foregoing, it is an object of the present disclosure to provide a knot forming device capable of easily and reliably forming knots through mechanical operations requiring only simple manipulations.

In order to attain the above and other objects, the present disclosure provides a knot forming device configured to form a knot in a tying medium. The knot forming device includes: a base part; a first arm; a second arm; a switching mechanism; a first loop retaining member; a first moving portion; and an operating part. The base part extends in a first direction. The first arm is disposed on the base part and has a first retaining member. The first retaining member is configured to detachably retain a first position of the tying medium at a first retaining position. The second arm is disposed on the base part and has a second retaining member. The second retaining member is configured to detachably retain the first position of the tying medium at a second retaining position instead of the first retaining member. The switching mechanism is configured to switch a retained state of the first position of the tying medium between a first state where the first position is retained by the first retaining member at the first retaining position and a second state where the first position is retained by the second retaining member at the second retaining position. The second arm functioning as the first loop retaining member is configured to retain a first loop around the second arm in a first path of the tying medium. The first path extends from the first retaining position through a second position and a third position to a fourth position of the tying medium. The second position of the tying medium intersects the third position of the tying medium as a result of the first loop such that the third position is downstream of the second position in a direction of the first path, and is closer to the first retaining position than the second position is to the first retaining position in the first path. The first moving portion is configured to move the first loop relative to the second arm in synchronism with the switching operation of the switching mechanism from the first state to the second state to thus change a relative positional relationship between the first loop and the first position of the tying medium on the first path. The operating part is configured to operate the switching mechanism and the first moving portion.

According to another aspect, the present disclosure provides a knot forming device configured to form a knot in a tying medium. The knot forming device includes: a base part; a first arm; a second arm; a switching mechanism; a first loop forming member; a first loop retaining member; a first moving portion; and an operating part. The base part extends in a predetermined direction. The first arm is disposed on the base part and has a first retaining member. The first retaining member is configured to detachably retain a first position of the tying medium at a first retaining position. The second arm is disposed on the base part and has a second retaining member. The second retaining member is configured to detachably retain the first position of the tying medium at a second retaining position instead of the first retaining member. The switching mechanism is configured to switch a retained state of the first position of the tying medium between a first state where the first position is retained by the first retaining member at the first retaining position and a second state where the first position is retained by the second retaining member at the second retaining position. The first loop forming member is configured to form a first loop around the second arm in a first path of the tying medium. The first path extends from the first retaining position through a second position and a third position to a fourth position of the tying medium. The second position of the tying medium intersects the third position of the tying medium as a result of the first loop such that the third position is downstream of the second position in a direction of the first paths and is closer to the first retaining position than the second position is to the first retaining position in the first path. The second arm functions as the first loop retaining member. The first loop retaining member is configured to retain the first loop. The first moving portion is configured to move the first loop relative to the second arm in synchronism with the switching operation of the switching mechanism from the first state to the second state to thus change a relative positional relationship between the first loop and the first position of the tying medium on the first path. The operating part is configured to operate the switching mechanism and the first moving portion.

According to still another aspect, the present disclosure provides a knot forming device configured to form a knot in a tying medium. The knot forming device includes; a base part; a first arm; a second arm; a switching mechanism; a first loop retaining member; a first moving portion; and an operating part. The base part extends in a first direction. The first arm is disposed on the base part and has a first retaining member. The first retaining member is configured to detachably retain a first position of the tying medium at a first retaining position. The second arm is disposed on the base part and has a second retaining member. The second retaining member is configured to detachably retain the first position of the tying medium at a second retaining position instead of the first retaining member. The switching mechanism is configured to switch a retained state of the first position of the tying medium between a first state where the first position is retained by the first retaining member at the first retaining position and a second state where the first position is retained by the second retaining member at the second retaining position. The second arm functioning as the first loop retaining member is configured to retain a first loop prewapped around the second arm in a first path of the tying medium. The first path extends from the first retaining member through a second position and a third position to a fourth position of the tying medium. The second position of the tying medium intersects the third position of the tying medium as a result of the first loop such that the third position is downstream of the second position in a direction of the first path, and is closer to the first retaining position than the second position is to the second retaining position in the first path. The first moving portion is configured to move the first loop relative to the second arm in synchronism with the switching operation of the switching mechanism from the first state to the second state to thus change a relative positional relationship between the first loop and the first position of the tying medium on the first path. The operating part is configured to operate the switching mechanism and the first moving portion.

BRIEF DESCRIPTION OF THE DRAWINGS

The particular features and advantages of the disclosure as well as other objects will become apparent from the following description taken in connection with the accompanying drawings, in which:

FIG. 8 is a perspective view showing the first arm of the knot forming device at the closed position and a needle in a released state, from which a guide cover is omitted;

FIG. 9 is a perspective view showing the first arm of the knot forming device at the closed position and the needle in a locked state, from which the guide cover is omitted;

FIG. 10 is an enlarged perspective view illustrating a structure of the first arm of the knot forming device according to the first embodiment;

DETAILED DESCRIPTION

Figure 1:
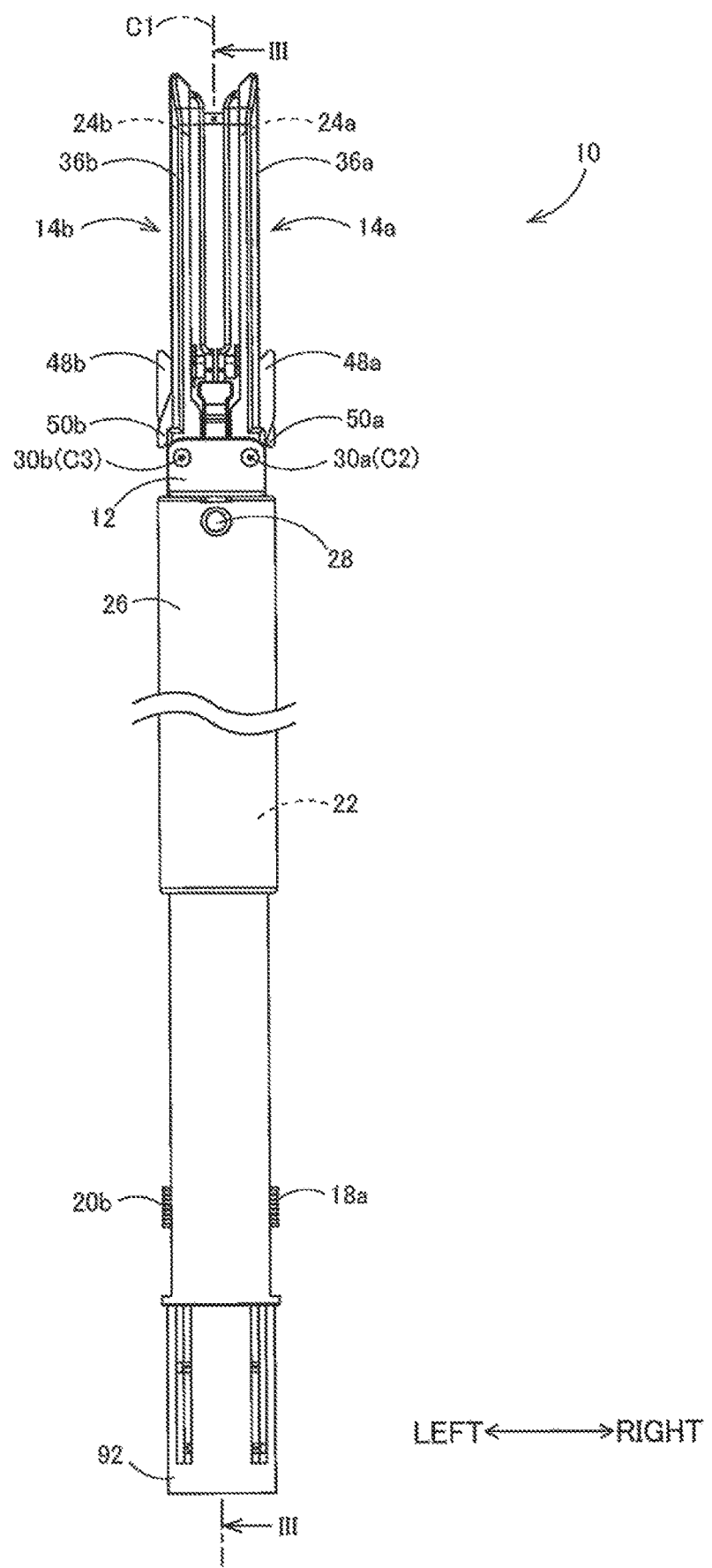
FIG. 1 is a front view showing a knot forming device according to a first embodiment of the present disclosure when a first arm and a second arm are in a closed state, from which a rotary operating member is omitted.

A knot forming device according to embodiments be described while referring to the accompanying drawings wherein like parts and components are designated by the same reference numerals to avoid duplicating description.

First Embodiment

Figure 2:
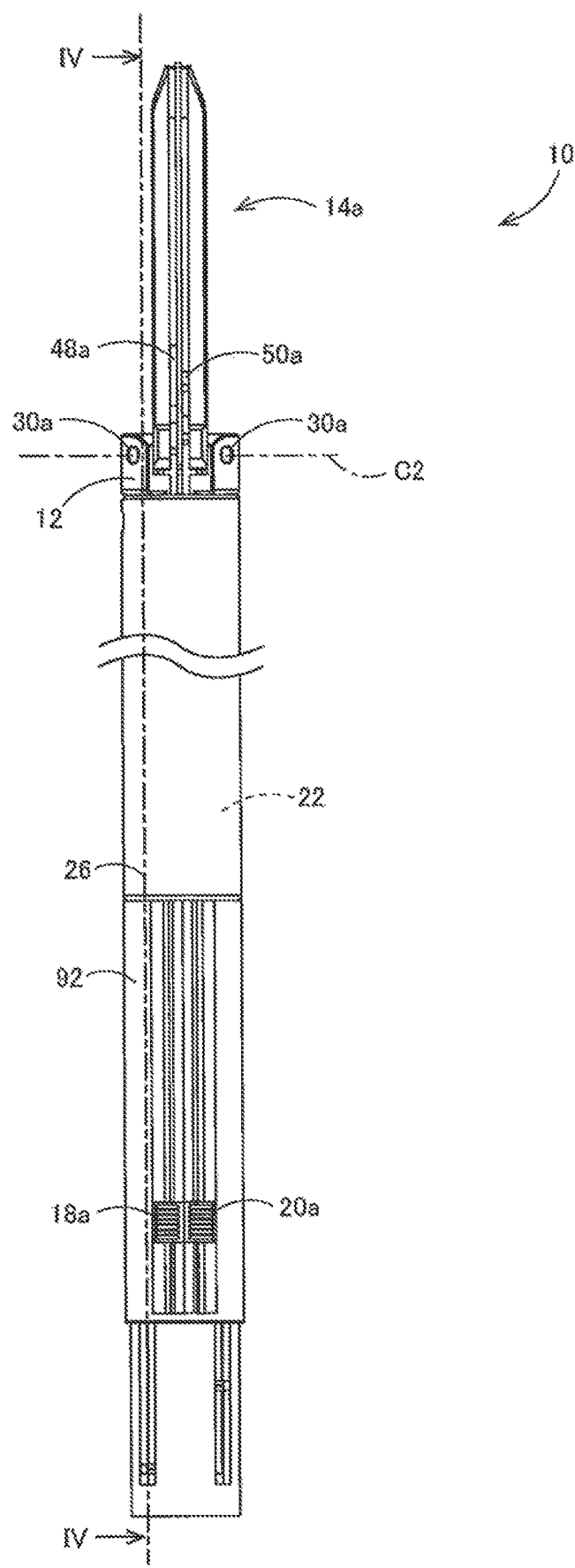
FIG. 2 is a right side view showing the knot forming device when the first arm and the second arm are in the closed state in the first embodiment.
Figure 3:
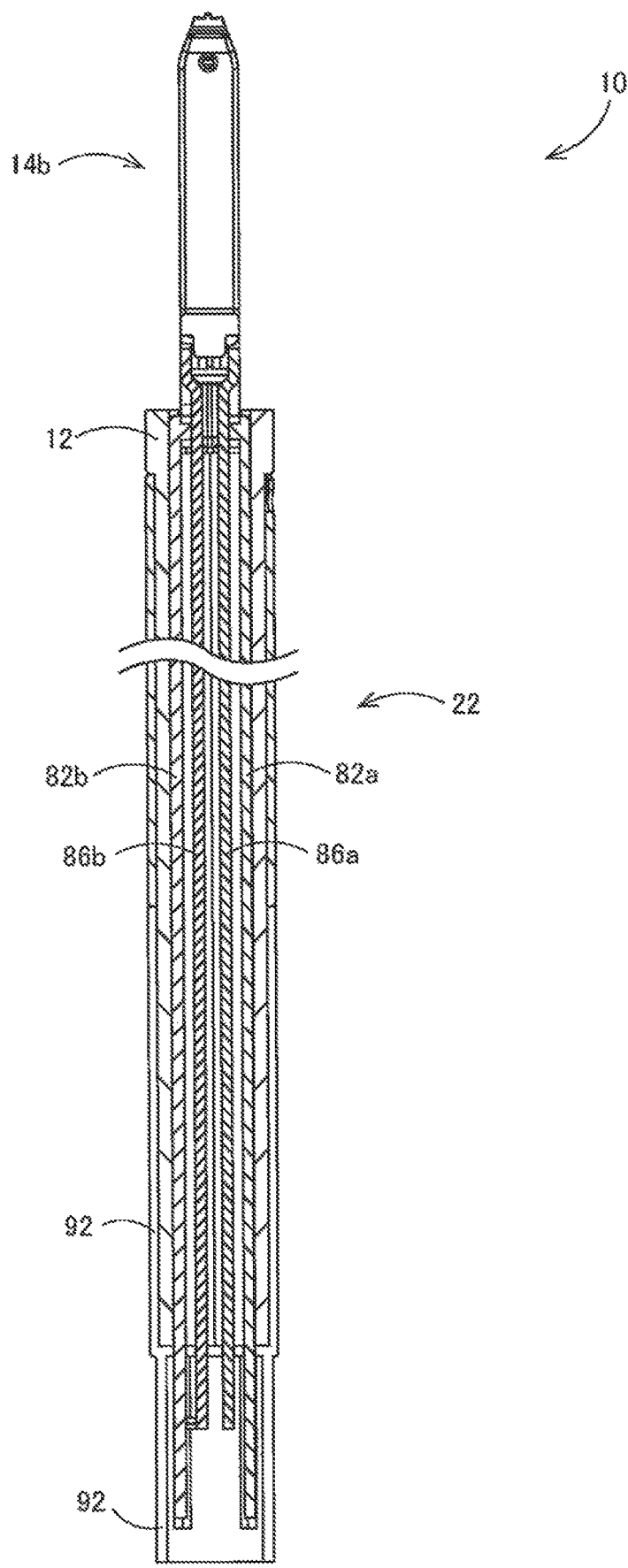
FIG. 3 is a vertical cross-sectional view of the knot forming device taken along a plane III-III of FIG. 1 in the first embodiment.
Figure 4:
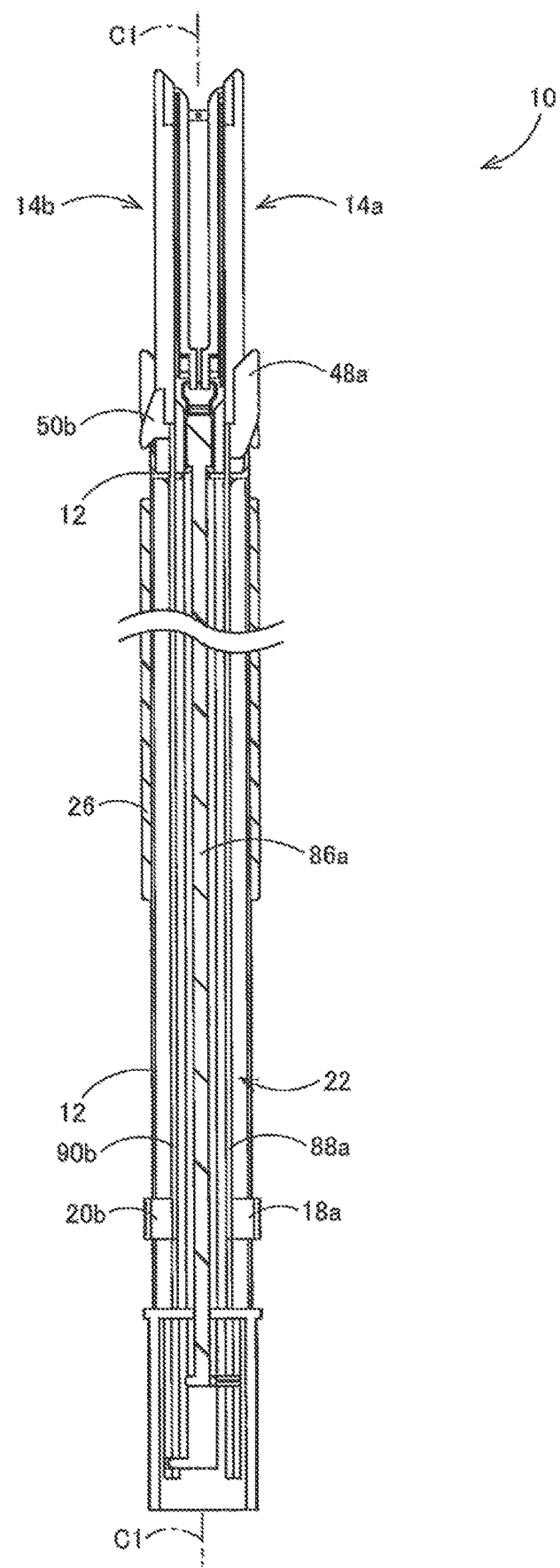
FIG. 4 is a vertical cross-sectional view of the knot forming device taken along a plane IV-IV of FIG. 2 in the first embodiment.

As shown in the front view of FIG. 1, the right side view of FIG. 2, and the vertical cross-sectional views of FIGS. 3 and 4, a knot forming device 10 is provided with a cylindrical elongate base member 12; a first arm 14a and a second arm 14b disposed on the distal end of the elongate base member 12 so as to be capable of opening and closing relative to each other; a rotary operating member 16 disposed on the proximal end of the elongate base member 12 so as to be capable of rotating about a central axis C1 of the elongate base member 12; four linear operating members 18a, 20a, 18b, and 20b disposed on the proximal end of the elongate base member 12 and capable of moving linearly along the central axis C1 of the elongate base member 12; and an operating force transmission mechanism 22 disposed inside the elongate base member 12 for transmitting the operating force of the rotary operating member 16 and the operating forces of the linear operating members 18a and 20a and linear operating members 18b and 20b. The operating force transmission mechanism 22 transmits the operating force of the rotary operating member 16 to the first arm 14a and second arm 14b for opening and closing the same and transmits the operating force of the rotary operating member 16 to a first needle locking mechanism 24a and a second needle locking mechanism 24b disposed respectively on the first arm 14a and second arm 14b for switching the state of a needle 52 between a locked state and a released state. The operating force transmission mechanism 22 also transmits the operating threes of the linear operating members 18a, 20a, 18h, and 20b to a first movable member 48a and a third movable member 50a (described later) disposed on the rear surface of the first arm 14a, and to a second movable member 48b and a fourth movable, member 50b (described later) disposed on the rear surface of the second arm 14b for moving these members along the longitudinal direction of the first arm 14a and second arm 14b.

Figure 5:
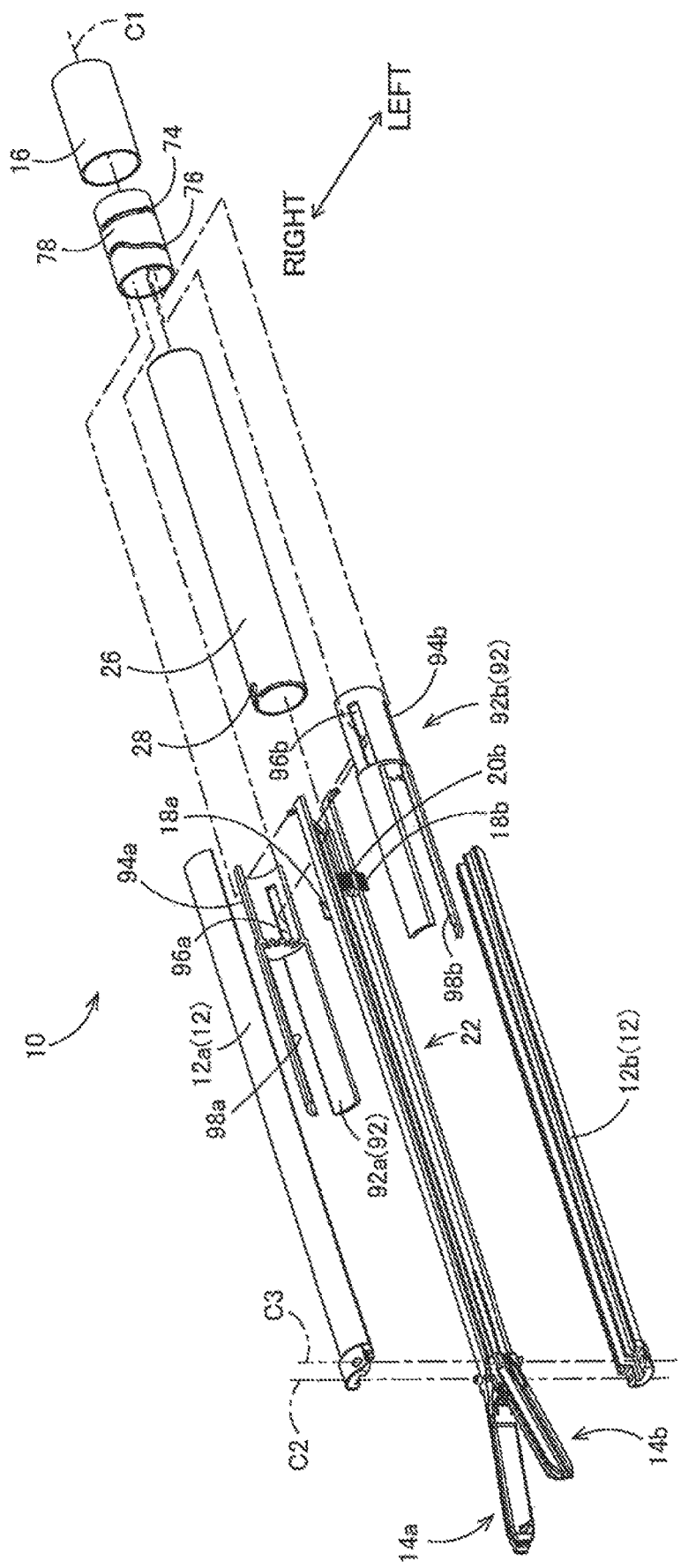
FIG. 5 is an exploded perspective view illustrating a structure of the knot forming device according to the first embodiment.

As shown in the exploded perspective view of FIG. 5, the elongate base member 12 is configured of a pair of partial cylindrical members 12a and 12b having semicircular cross sections that form a cylindrical shape when assembled and fixed together. An outer sleeve 26 is fitted around the outer circumference of the elongate base member 12 so as to be capable of rotating relative to the elongate base member 12 but incapable of moving along the central axis C1 of the elongate base member 12. The outer sleeve 26 functions as a loop forming member and a rotating member that wraps a thread-like member L around the outer circumference of the first arm 14a and second arm 14b. A thread guiding hole 28 is formed in the distal end of the outer sleeve 26. The thread guiding hole 28 is a through-hole for guiding the thread-like member L passed therethrough. In the present embodiment, the elongate base member 12 functions as a base part, and the rotary operating member 16 and linear operating members 18a, 20a, 18b, and 20b function as operating parts. Note that the rotary operating member 16 has been omitted from FIGS. 1 through 4, while the thread-like member L functioning as the tying medium has been omitted from FIGS. 1 through 9. The thread-like member L contacts the outer sleeve 26 on the edge of the thread guiding hole 28. The portion of the thread-like member L passing through the thread guiding hole 28 will be considered the fourth position of the tying medium in the present embodiment. Further, while the thread guiding hole 28 is a through-hole in the present embodiment, the thread guiding hole may have an open shape, such as a C-shaped groove, provided that the thread guiding hole 28 is capable of guiding the thread-like member L.

A pair of support holes 30a and a pair of support holes 30b are also formed in the distal end of the elongate base member 12. The support holes 30a are spaced apart a prescribed distance along a central axis C2 orthogonal to the plane within which the first arm 14a and second arm 14b open and close. The support holes 30b are positioned along a central axis C3 parallel to the central axis C2. The first arm 14a is rotatably supported by the support holes 30a and is capable of rotating about the central axis C2, while the second arm 14b is rotatably supported by the support holes 30b and is capable of rotating about the central axis C3. Since the first arm 14a and second arm 14b have a similar configuration, the following description will focus solely on the first arm 14a, where the letter "a" is appended to reference numbers associated with the first arm 14a while the letter "b" is appended to the same reference numerals associated with the second arm 14b.

The first arm 14a includes an arm body 36a. The arm body 36a integrally possesses a pair of protruding shafts 32a that are fitted respectively into the pair of support holes 30a, and an open/close coupling arm 34a. With this configuration, the first arm 14a and arm body 36a are rotatably supported by the pair of support holes 30a so that the first arm 14a can rotate about the central axis C2 passing through the center of the support holes 30a between an open position shown in FIG. 6 and a closed position shown in FIG. 7.

Further, the first needle locking mechanism 24a provided on the first arm 14a includes a guide cover 38a a locking plate 40a, a T-shaped bar supporting part 42a, and an elongated locking operation bar 46a provided on the arm body 36a. The guide cover 38a is fixed to the arm body 36a so as to cover the entire opposing surface on the second arm 14b side of the arm body 36a, while a slight gap is formed between the guide cover 38a and opposing surface of the arm body 36a. The locking plate 40a is accommodated between the guide cover 38a and the opposing surface of the arm body 36a and can move along the longitudinal direction of the first arm 14a. The T-shaped bar supporting part 42a is formed on the proximal end of the guide cover 38a, with a smaller width dimension than the arm body 36a, and is offset from the guide cover 38a toward the second arm 14b side. The locking operation bar 46a has a longitudinal dimension equivalent to the width dimension of the arm body 36a. The longitudinal center portion of the locking operation bar 46a is rotatably supported on the inner side of the T-shaped bar supporting part 42a, with both longitudinal ends of the locking operation bar 46a exposed outside the T-shaped bar supporting part 42a and a first end of the locking operation bar 46a is engaged in an engaging recessed part 44a formed in the locking plate 40a. The first end of the locking operation bar 46a engaged in the engaging recessed part 44a has a protrusion (not shown). With this protrusion engaged in the engaging recessed part 44a, the locking operation bar 46a is placed in a slanted orientation that reflects whether the locking plate 40a is in a distal side position or a proximal side position relative to the first arm 14a. For example, when the locking plate 40a is in the proximal side position relative to the first arm 14a, as shown in FIG. 8, the locking operation bar 46a is placed in a slanted orientation in which the first end is nearer the proximal side, and the second end is nearer the distal side. In this position, the needle 52 is in a released state. Conversely, when the locking plate 40a is in the distal side position relative to the first arm 14a, as shown in FIG. 9, the locking operation bar 46a is placed in a sloped orientation in which the second end of the locking operation bar 46a is nearer the proximal side and the first end is nearer the distal side. In this orientation, the needle 52 is in a locked state. The T-shaped bar supporting part 42a has a stopper function for alternately contacting each end of the locking operation bar 46a, whereby the locking operation bar 46a is alternately positioned in the distal side position and the proximal side position relative to the first arm 14a.

The first needle locking mechanism 24a provided on the first arm 14a having the structure described above and the second needle locking mechanism 24b provided on the second arm 14b having an identical structure constitute a switching mechanism for transferring the needle 52 back and forth between the first arm 14a and second arm 14b. To achieve this transfer, the first needle locking mechanism 24a or second needle locking mechanism 24b that is locking the corresponding end of the needle 52 is operated to release that end, while the other is operated to shift from the released state to the locked state on the corresponding end of the needle 52.

Figure 6:
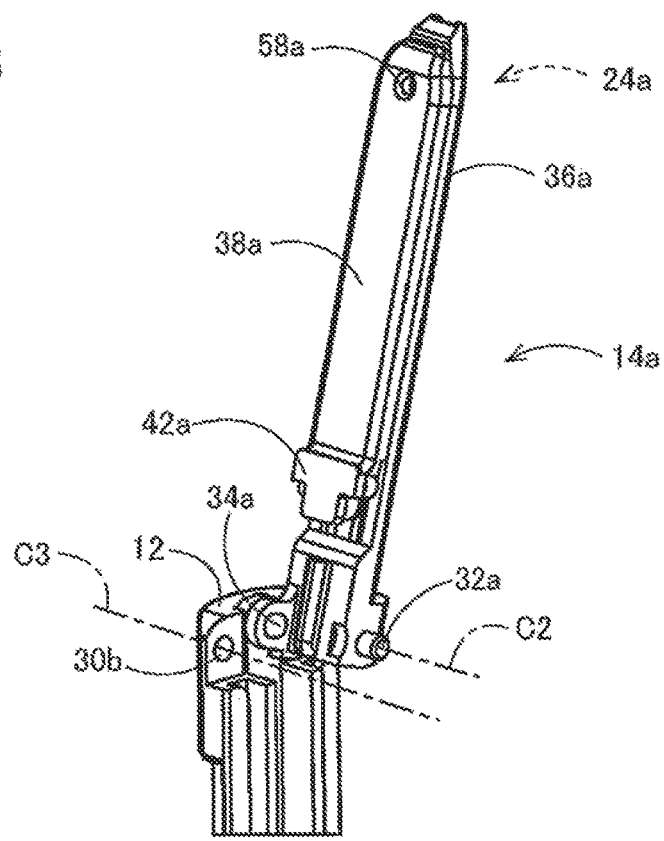
FIG. 6 is a perspective view showing the first arm of the knot forming device at an open position in the first embodiment.

FIG. 6 shows the first arm 14a in the open state. FIGS. 1 through 4 and 7 show the first arm 14a in the closed state. FIG. 8 shows the needle 52 in the released state. FIG. 9 shows the needle 52 in the locked state. The needle 52 has annular engaging grooves 53 and 54 formed one on each longitudinal end of the needle 52, and a through-hole 55 formed in the longitudinal center of the needle 52 (see FIG. 11). A thread-like member L serving as the tying medium is passed through the through-hole 55. Since the end of the needle 52 in which the engaging groove 53 is formed is retained in the first arm 14a in FIGS. 8 and 9, the engaging groove 53 does not appear in these drawings. In the present embodiment, the thread-like member L is fixed to the needle 52 by a process called crimping in which an external force is applied for collapsing the through-hole 55 while the thread-like member L is inserted therethrough. However, the thread-like member L may be fixed to the needle 52 using adhesive or the like or by tying a knot in the end of the thread-like member L that is larger than the through-hole 55. Further, while both ends of the needle 52 are tapered to a point in the present embodiment, the ends of the needle 52 may be formed in different shapes instead.

Figure 11:
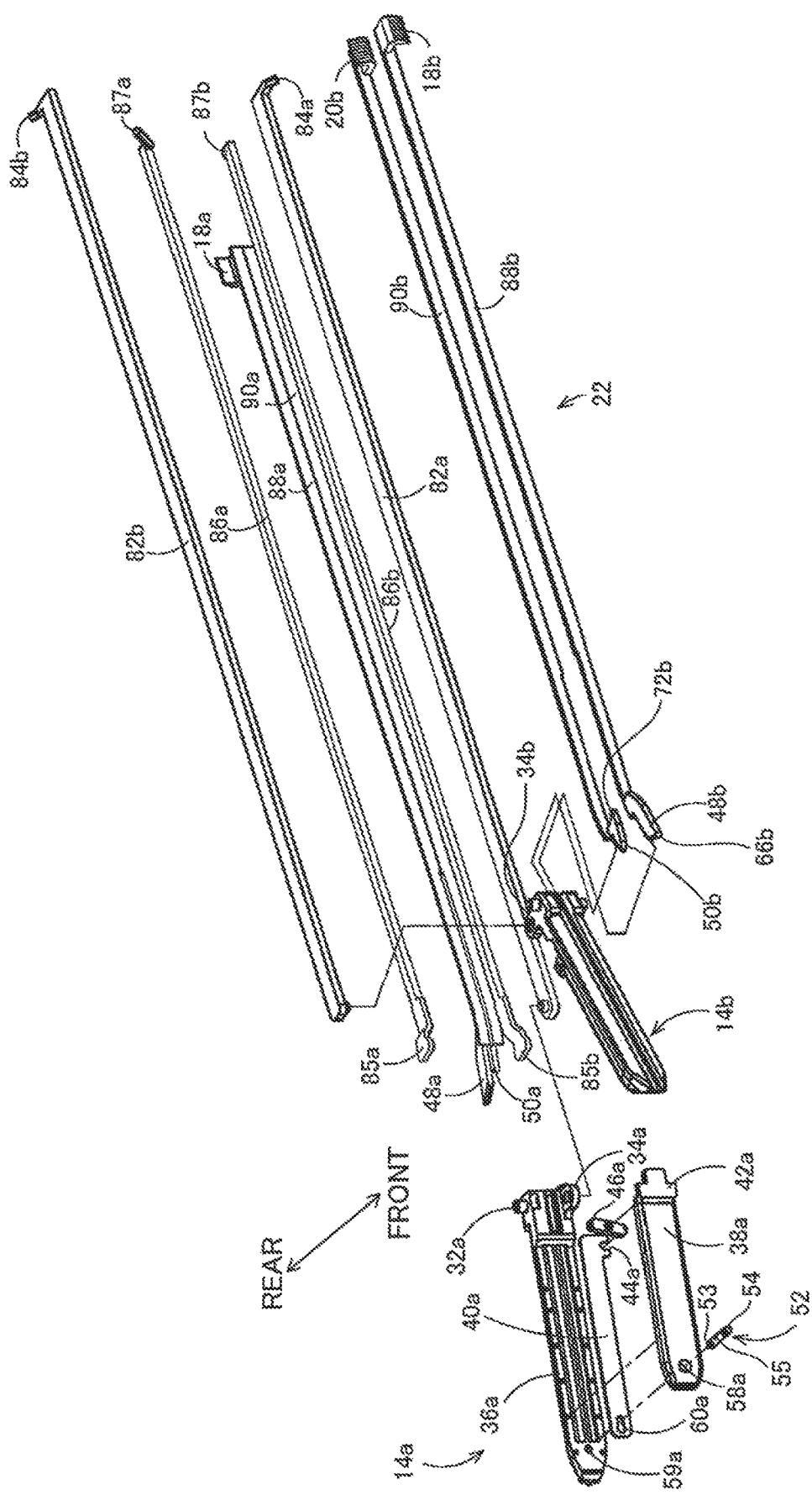
FIG. 11 is an exploded perspective view illustrating a structure of an operating force transmission mechanism of the knot forming device according to the first embodiment.

A portion of the exploded perspective view in FIG. 11 is enlarged and shown in greater detail in FIG. 10. As shown in the drawings, a receiving hole 59a face FIG. 11) for receiving an end of the needle 52 is formed in the opposing surface of the arm body 36a at a position near the distal end of the sane, and a through-hole 58a through which the needle 52 can pass is formed in the guide cover 38a at a position corresponding to this receiving hole 59a. Further, an engaging hole 60a is formed in the locking plate 40a at a position corresponding to the receiving hole 59a and through-hole 58a. The engaging hole 60a has a shape for engaging with the engaging groove 53 of the needle 52 to lock the needle 52 when the locking plate 40a is in the distal side position, and to allow the needle 52 to pass therethrough when the locking plate 40a is in the proximal side position. That is, the engaging hole 60a has a keyhole shape formed of a circular hole having a larger diameter than the outer diameter of the needle 52 coupled with a rectangular notch having a width dimension that is larger than the inner diameter of the engaging groove 53 formed in the needle 52 and smaller than the outer diameter of the needle 52.

A first guide groove 62a and a second guide groove 64a are formed in the rear surface of the arm body 36a. The first guide groove 62a and second guide groove 64a are formed in parallel along the longitudinal direction of the first arm 14a and function to guide a first movable member 48a, said a third movable member 50a, respectively. A sloped receiving surface 66a is formed on the first movable member 48a. The sloped receiving surface 66a slopes away from the fast arm 14a in a direction toward the distal end of the same, and receives the thread-like member L wrapped around the first arm 14a from the proximal side thereof. Further, an anchoring surface 72a is formed on the third movable member 50a. The anchoring surface 72a slopes so as to approach the first arm 14a in a direction toward the distal end of the same and functions to anchor the thread-like member L from the distal side thereof. The thread-like member L anchored on the anchoring surface 72a of the third movable member 50a, and specifically the portion of the thread-like member L wrapped around the first arm 14a and positioned between the anchoring surface 72a and the sloped receiving surface 66a of the first movable member 48a, can be enclosed and retained thereby. The portion of the head-like member L supported on the sloped receiving surface 66a constitutes a seventh position in the present disclosure. Similarly, the thread-like member L anchored on an anchoring surface 72b of a fourth movable member 50b, and specifically the portion of the thread-like member L wrapped around the second arm 14b and positioned between the anchoring surface 72b and the sloped receiving surface 66b of the second movable member 48b, can be enclosed and retained thereby (see FIG. 11). The portion of the thread-like member L supported on the sloped receiving surface 66b constitutes an eighth position in the present disclosure. When tightening the knot in the thread-like member L, the first movable member 48a or the third movable member 50a and first movable member 48a function as first guide members that guide the thread-like member L so that the thread-like member L on both sides of the knot form an angle approaching 180 degrees.

The rotary operating member 16 has a cylindrical shape. A cylindrical grooved cam 78 is integrally provided on the inner circumferential side surface of the rotary operating member 16. An arm opening/closing cam groove 74 for effecting the opening and closing operations of the first arm 14a and second arm 14b, and a needle locking cam groove 76 for effecting the locking and releasing operations of the needle 52 are formed in rings in the cylindrical grooved cam 78. While the cylindrical grooved cam 78 is formed integrally with the rotary operating member 16, the cylindrical grooved cam 78 and rotary operating member 16 are shown separately in FIG. 5 for convenience. Further, the linear operating members 18a, 20a, 18b, and 20b are disposed on side surfaces of the elongate base member 12, as illustrated in FIGS. 1 and 2, for example, and are capable of being operated in a direction parallel to the central axis C1 of the elongate base member 12.

As shown in the vertical cross-sectional views of FIGS. 3 and 4 and the exploded perspective view of FIG. 11, the operating force transmission mechanism 22 is provided with a first open/close operating force transmission link 82a and a second open/close operating force transmission link 82b. The distal end of the first open/close operating force transmission link 82a is rotatably coupled to the open/close coupling arm 34a for transmitting an open/close operating force to the open/close coupling arm 34a in order to move the first arm 14a between its open position and closed position. The proximal end of the first open/close operating force transmission link 82a has a cam engaging part 84a that protrudes at a right angle to the longitudinal direction of the first open/close operating force transmission link 82a and engages with the arm opening/closing cam groove 74 (see FIG. 5). The distal end of the second open/close operating force transmission link 82b is rotatably coupled to an open/close coupling arm 34b for transmitting an open/close operating force to the open/close coupling arm 34b in order to move the second arm 14b between its open position and closed position. The proximal end of the second open/close operating force transmission link 82b has a cam engaging part 84b that protrudes at a right angle to the longitudinal direction of the second open/close operating force transmission link 82b and engages with the arm opening/closing cam groove 74. With this configuration, when an operation of the rotary operating member 16 causes the cam engaging part 84a of the first open/close operating force transmission link 82a to pass through the segment of the arm opening/closing cam groove 74 in which the curved cam line chances toward the distal side of the elongate base member 12, the first open/close operating force transmission link 82a is moved toward the distal end of the elongate base member 12. When the first open/close operating force transmission link 82a moves toward the distal end of the elongate base member 12, the first arm 14a is rotated toward its open position. FIG. 6 shows the first arm 14a after having rotated toward its open position.

Figure 7:
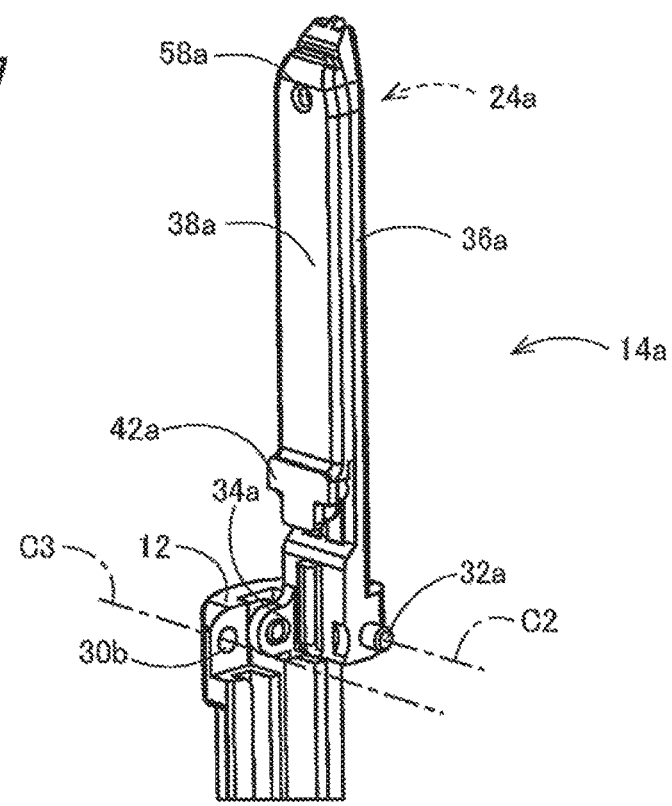
FIG. 7 is a perspective view showing the first arm of the knot forming device at a closed position in the first embodiment.

Conversely, when the rotary operating member 16 is operated such that the cam engaging part 84a of the first open/close operating force transmission link 82a passes through the segment of the arm opening/closing cam groove 74 in which the curved cam line changes toward the proximal side of the elongate base member 12, the first open/close operating force transmission link 82a is moved toward the proximal end of the elongate base member 12. In this way, when the first open/close operating force transmission link 82a is moved toward the proximal end of the elongate base member 12, the first arm 14a is rotated toward its closed position. FIG. 7 shows the first arm 14a when it has been rotated toward its closed position.

As with the first open/close operating force transmission link 82a of the first arm 14a, the second open/close operating force transmission link 82b of the second arm 14b is moved toward the distal end and proximal end of the elongate base member 12 together with the first open/close operating force transmission link 82a in association with the operation of the rotary operating member 16. In this way, the first arm 14a and second arm 14b are placed in their open states and closed states as a pair.

Figure 12:
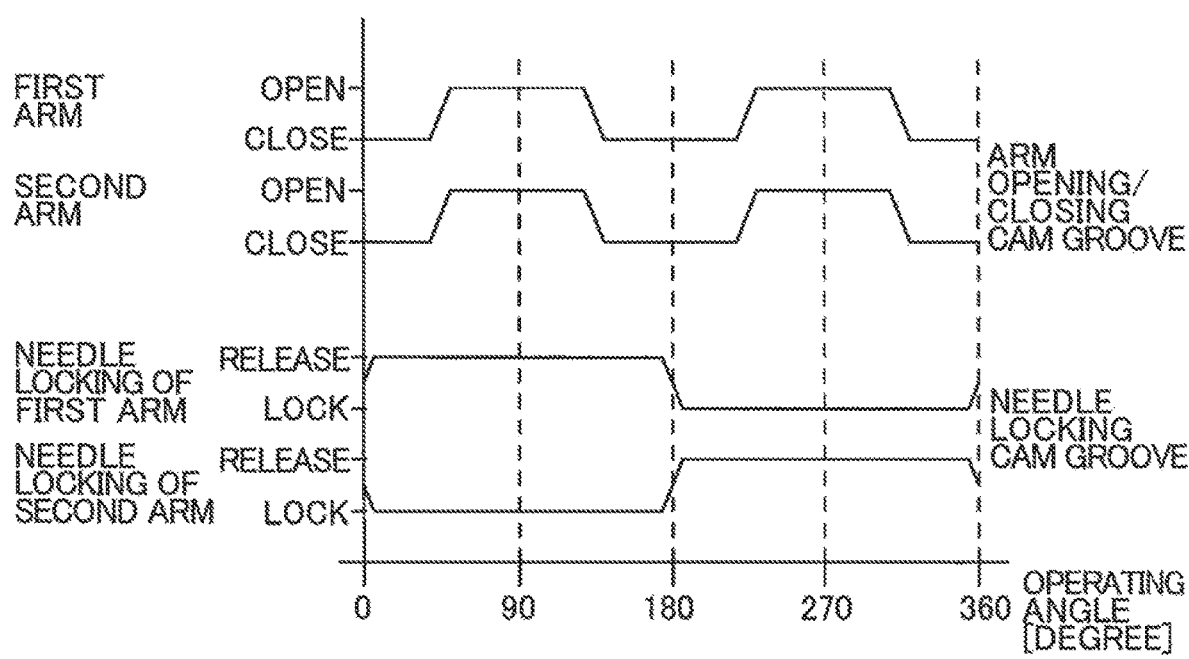
FIG. 12 is a chart illustrating a relationship between an operating angle of a rotary operating member of the knot forming device, and opening and closing operations for the first arm and the second arm and a locking and releasing operations for the needle in the first embodiment.

The operating tierce transmission mechanism 22 is further provided with a first pushrod 86a and a second pushrod 86b for transferring the needle 52 between the first arm 14a and second arm 14b when the first arm 14a and second arm 14b are placed in their closed state. The first pushrod 86a has a T-shaped lifting part 85a on the distal end thereof, and a cam engaging part 87a on the proximal end thereof. The T-shaped lifting part 85a contacts and rotates the first ends of the locking operation bars 46a and 46b (not shown). The cam engaging part 87a protrudes at a right angle to the longitudinal direction of the first pushrod 86a and engages with the needle locking cam groove 76. The second pushrod 86b has a T-shaped lifting part 85b on the distal end thereof, and a cam engaging part 87b on the proximal end thereof. The T-shaped lifting part 85b contacts and rotates the second ends of the looking operation bars 46a and 46b (not shown). The earn engaging part 87b protrudes at a right angle to the longitudinal direction of the second posh rod 86b and engages with the needle locking cam groove 76. As shown in FIG. 12, the needle locking cam groove 76 has a curved cam line that is shaped such that one of the first pushrod 86a and second pushrod 86b protrudes toward the distal side of the elongate base member 12 while the other is drawn toward the proximal side of the elongate base member 12. FIG. 8 shows the state of the needle 52 in the first an 14a after being released by the locking plate 40a. At this time, the needle 52 is engaged by the locking plate 40b in the second arm 14b (not shown). FIG. 9 shows the state of the needle 52 engaged by the locking plate 40a in the first arm 14a. At this time, the needle 52 is not engaged but released by the locking plate 40b in the second arm 14b (not shown). In this way, the needle 52 transitions from a state in which a first end of the needle 52 is retained in the first arm 14a and a second end of the needle 52 is released from the second arm 14b to a state in which the second end of the needle 52 is retained in the second arm 14b and the first end of the needle 52 is released from the first arm 14a, for example, while the first arm 14a and second arm 14b are closed. In other words, the needle 52 is transferred between the first arm 14a and second arm 14b.

In the present embodiment, the receiving hole 59a in the arm body 36a, the through-hole 58a in the guide cover 38a, and the engaging hole 60a formed in the locking plate 40a of the first arm 14a combine to function as a first retaining member that retains the first end of the needle 52. Further, the receiving hole 59b (not shown) in the arm body 36b, the through-hole 58b (not shown) in the guide cover 38b, and the engaging hole 60b (not show) formed in the locking plate 40b of the second arm 14b combine to function as a second retaining member that retains the other end of the needle 52.

The operating force transmission mechanist 22 is also provided with elongated first flexible connecting plates 88a and 88b, and second flexible connecting plates 90a and 90b. The first flexible connecting plates 88a and 88b and second flexible connecting plates 90a and 90b perform a thread removing operation to move the thread-like member L wrapped around the first arm 14a and/or second arm 14b off the distal end thereof, or a thread anchoring operation for positioning the thread-like member L on the distal end of the first arm 14a and/or second arm 14b and anchoring the thread-like member L thereon when the first arm 14a and second arm 14b are in their open states. The first flexible connecting plates 88a and 88b are formed of an elastic deformable material or a flexible material such as a relatively in plate-like spring steel or a hard plastic plate, for example, and are capable of deforming by bending in the thickness direction. For the first arm 14a, the first flexible connecting plate 88a has the first movable member 48a on its distal end and the linear operating member 18a on its proximal end, while the second flexible connecting plate 90a has the third movable member 50a on its distal end and the linear operating member 20a on its proximal end. For the second arm 14b, the first flexible connecting plate 88b has the second movable member 48b on its distal end and the linear operating member 18b on its proximal end, while the second flexible connecting plate 90b has the fourth movable member 50b on its distal end and the linear operating member 20b on its proximal end. Opening and closing of the first arm 14a and second arm 14b is allowed through the elastic deformation of the first flexible connecting plates 88a and 88b and second flexible connecting plates 90a and 90b. Note that the operations of the first movable member 48a, third movable member 50a, second movable member 48b, and fourth movable member 50b may be effected through manual operations of the linear operating members 18a and 20a and linear operating members 18b and 20b or through automatic operations using an actuator such as a pneumatic cylinder or an electric cylinder. In the case of automatic operations, the actuator may be activated in response to a signal produced by the rotary operation of the rotary opening member 16. Alternatively, a control panel section or the like may be provided separately for automatic operations. In this case, the control panel section corresponds to the operating part of the present disclosure.

As shown in FIG. 5, a cylindrical receiving member 92 is disposed in the elongate base member 12 on the proximal end thereof. As shown in FIG. 5, the receiving member 92 has a cylindrical shape configured by assembling and fixing together a pair of partial receiving members 92a and 92b having semicircular cross sections. The receiving member 92 supports the proximal ends of the first open/close operating force transmission link 82a and second open/close operating force transmission link 82b, i.e., the ends on the rotary operating member 16 side, so that the first open/close operating force transmission link 82a and second open/close operating force transmission link 82b can move along the longitudinal direction of the receiving member 92. The receiving member 92 is also formed with a pair of elongated guide holes 94a and 94b that penetrate the outer circumferential wall of the receiving member 92. The guide holes 94a and 94b are used to guide the earn engaging parts 84a and cam engaging parts 84b disposed on proximal ends of the corresponding first open/close operating force transmission 82a and second open/close operating force transmission link 82b along the longitudinal direction of the elongate base member 12. The receiving member 92 also supports the proximal ends of the first pushrod 86a and second pushrod 86b so that the first pushrod 86a and second pushrod 86b can move along the longitudinal direction of the receiving member 92. The receiving member 92 is also formed with a pair of elongated guide holes and 96b that penetrate the outer circumferential surface of the receiving member 92. The guide holes 96a and 96b are used to guide the cam engaging parts 87a and 87b disposed on the ends of the corresponding first pushrod 86a and second pushrod 86b along the longitudinal direction of the elongate base member 12. The receiving member 92 is also provided with a pair of elongated guiding notches 98a and 98b that penetrate the outer circumferential wall of the receiving member 92 and are open on the distal end of the receiving member 92. The guiding notch 98a is used to guide the linear operating member 18a and linear operating member 20a in the longitudinal direction of the elongate base member 12, while the guiding notch 98b is used to guide the linear member 18b and linear operating member 20b along the longitudinal direction of the elongate base member 12.

FIG. 12 is a chart illustrating the states of the first arm 14a, second arm 14b, and needle 52 as the following two operations are executed in a prescribed order for forming a knot by rotating the rotary operating member 16: locking and releasing operations for the needle 52 performed with the kicking plate 40a and locking plate 40b, and opening and closing operations for the first arm 14a and second arm 14b. The horizontal axis in the chart of FIG. 12 represents the angle through which the rotary operating member 16 is rotated in a right-handed turn from the orientation in FIG. 1. FIG. 6 shows the position of the first arm 14a after the rotary operating member 16 has been rotated about 135 degrees from the point of origin on the horizontal axis in FIG. 12, and FIG. 7 shows the position of the first arm 14a after the rotary operating member 16 has been rotated approximately 45 degrees. This operation of rotating the rosary operating member 16 may be a manual operation or a remote operation using the drive of a motor to rotate the rotary operating member 16.

As shown in FIG. 12, the operation for rotating the rotary operating member 16 is performed with the knot forming device 10 having the above structure in order to implement the operations of opening and closing the first arm 14a and second as 14b and transferring the needle 52 between the first arm 14a and second arm 14b. Other operations performed in relation to these operations are a wrapping operation for wrapping the thread-like member L around the first arm 14a and second arm 14b through the operation of the outer sleeve 26, and a thread removing operation performed by manually operating either the linear operating members 18a and 20a or the linear operating members 18b and 20b. These operations semiautomatically form a knot in the thread-like member L. Next, the operations of the knot forming device 10 according to the present embodiment will be described in greater detail with reference to FIGS. 13, 14, 15, and 16.

Figure 13:
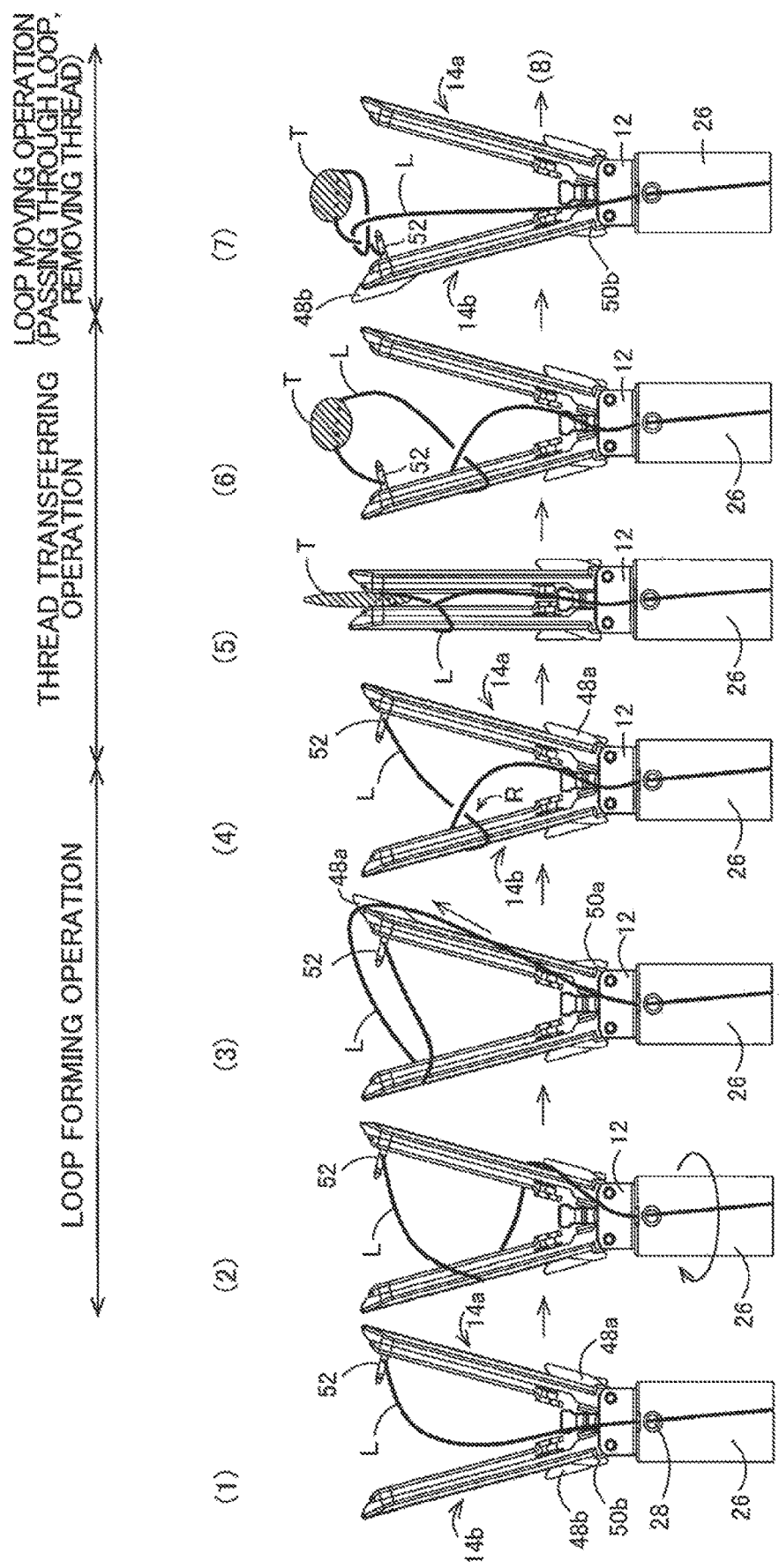
FIG. 13 is an explanatory diagram illustrating a part of steps in a knot forming operation performed by the knot forming device according to the first embodiment.

Step (1) in FIG. 13 shows the initial state of the knot forming device 10 in a knot forming operation. In this initial state, the first movable member 48a and third movable member 50a are positioned on the proximal end of the first arm 14a and the second movable member 48b and fourth movable member 50b are positioned on the proximal end of the second arm 14b, while the first arm 14a and second arm 14b are in an open state for the interval in which the operating angle of the rotary operating member 16 moves from 45 degrees to near 135 degrees. Further, the needle 52 is fixed in the first needle locking mechanism 24a of the first arm 14a and the thread-like member L fixed at one end to the needle 52 is passed through the thread guiding hole 28 of the outer sleeve 26. Next, steps in the loop forming operation shown in (2) through (4) of FIG. 13 are sequentially performed. Specifically, by rotating the outer sleeve 26 one left-handed turn from the initial state described above, the thread-like member L is wrapped around the outside of the first arm 14a and second arm 14b, as indicated in (2) of FIG. 13. As shown in (3) of FIG. 13, the first movable member 48a of the first arm 14a is moved from its proximal position to a distal position on the first arm 14a by the operation of the linear operating member 18a. As indicated in (4) of FIG. 13, the first movable member 48a is returned to the proximal end of the first arm 14a after the thread-like member L has passed off the distal end of the first arm 14a and entered between the first arm 14a and second arm 14b. When the opposite end of the thread-like member L is pulled in this state, a loop R for forming a knot is formed in the thread-like member L wrapped about the second arm 14b. While the outer sleeve 26 was rotated one turn in the present embodiment, the elongate base member 12, first arm 14a, and second arm 14b may instead be rotated relative to the outer sleeve 26, which remains stationary in the rotating direction.

Figure 17:
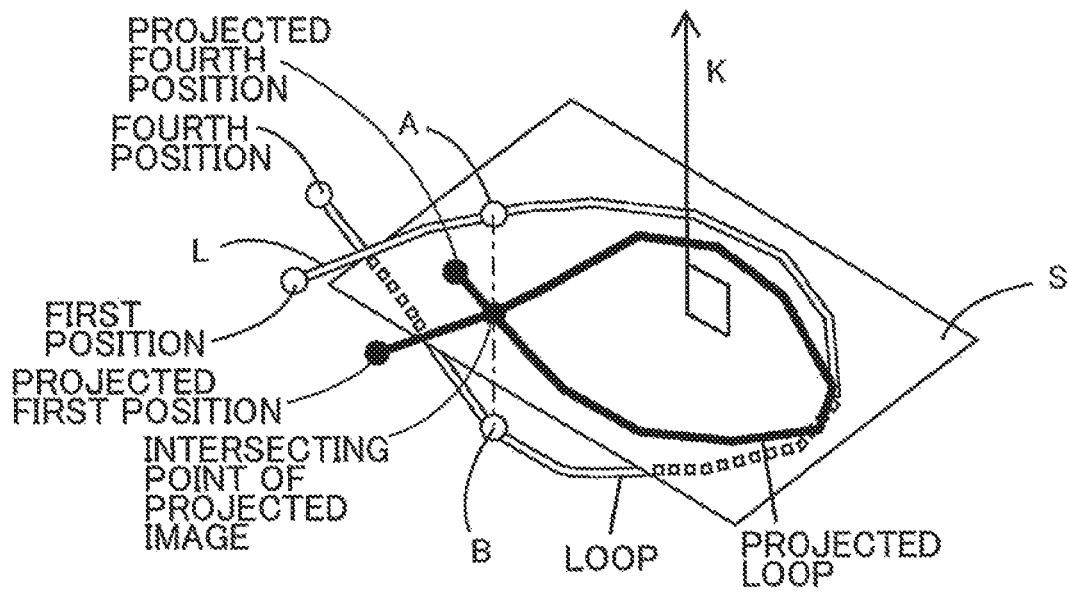
FIG. 17 is an explanatory diagram illustrating a definition of a loop by using that a projected image of a thread tike member projected onto a projecting surface S occupying a plane orthogonal to a virtual axis K forms a closed path.

The term "loop" in this description denotes the portion of the thread-like member L surrounding a certain axis when the thread-like member L encircles this axis at least one wrap, i.e., at least 360 degrees. Put another way, if an image of the thread-like member L projected onto a plane orthogonal to a certain axis intersects itself and the axis is present within the ring-like enclosed portion that includes this intersecting point of the projected image, the loop is the actual portion a the thread-like member L that produces the ring-like portion in the projected image. In order to form a knot, the end of the thread-like member L must pass through this loop formed in the thread-like member L. Here, "passing through" merely means that the loop and the end of the thread-like member L pass one another through relative movement along the axis defining the loop so that their relative positions in the axial direction are switched. However, only one of the two directions in which the end of the thread-like member L can pass through the loop succeeds in forming a knot, while the other direction does not. A knot is not formed when the end of the thread-like member L passes in the other direction because the loop disappears before the end of the thread-like member L can pass therethrough and is no longer a loop at the moment of passing. This concept will be described in greater detail with reference to FIG. 17. In FIG. 17, a loop defined by a virtual axis K is projected onto a projecting surface S occupying a plane orthogonal to the virtual axis K. When the projected image of the thread-like member L forms a closed path, the portion of the actual thread-like member L projected at the intersecting point of this closed path is a multilevel intersection configured of two positions on the thread-like member L, and specifically a second position (first intersecting position) A that is closer to a first position, which is a first end, of the member L, and a third position (second intersecting position) B that is farther from the first position. Here, a knot can be formed by passing the first position, i.e., the end of the thread-like member L being passed through the loop, in the direction from the third position B side to the second position A side relative to the loop; that is, the direction along the virtual axis K indicated by the arrow in FIG. 17. With respect to (4) in FIG. 13, it can be said that the loop is formed around the second 14b. In other words, if a first path is the path from a first retaining position (i.e., a position at which the first position of the thread-like member L fixed to the needle 52 is retained by the first needle locking mechanism 24a of the first arm 14a) to the fourth position of the thread-like member L along the device body configured of the first arm 14a and elongate base member 12, then the loop is formed around the first path.

Steps (5) and (6) in FIG. 13 show the sequence of steps in the thread transferring operation. That is, by continuing to rotate the rotary operating member 16 until the angle of the rotary operating member 16 passes through the area near 180 degrees, the first arm 14a and second arm 14b close around biological tissue T, as illustrated in (5) of FIG. 13. At this time, the second end of the needle 52, whose first end is locked in the first needle locking mechanism 24a of the first arm 14a, passes through the tissue T and is received and locked in the second needle locking mechanism 24b of the second arm 14b while the first end of the needle 52 lacked in the first needle locking mechanism 24a is released (unlocked). Next, the first arm 14a and second arm 14b are opened by continuing to rotate the rotary operating member 16 until its operating angle passes the area near 225 degrees. Step (6) in FIG. 13 shows the state of the first arm 14*a* and second arm 14*b* at this time.

In a topological sense, a knot is already formed at this stage by the closed path configured of the thread-like member L, first arm 14*a*, second arm 14*b*, and elongate base member 12. If an object can be formed in the same shape through continuous deformation, the shapes of the object before and after deformation are equivalent in topology. When a thread-like object forms a closed loop, the shape of the object is considered equivalent in topology if the object is deformed using only continuous deformation (called a Reidemeister move) and not discontinuous deformation, such as deformation achieved by passing the thread through itself or by once cutting the loop and crossing the cut threads to form another closed loop. In general, the topology of a thread forming a closed loop that does not contain a knot differs from the topology of a thread forming a closed loop that contains a knot. Thus, the statement that a knot is already formed in a topological sense means that the closed path formed by the thread-like member L, first arm 14*a*, second arm 14*b*, and elongate base member 12 can be modified through only continuous deformation into a shape in which a knot exists in only the portion of the closed path constituted by the thread-like member L.

Figure 14:
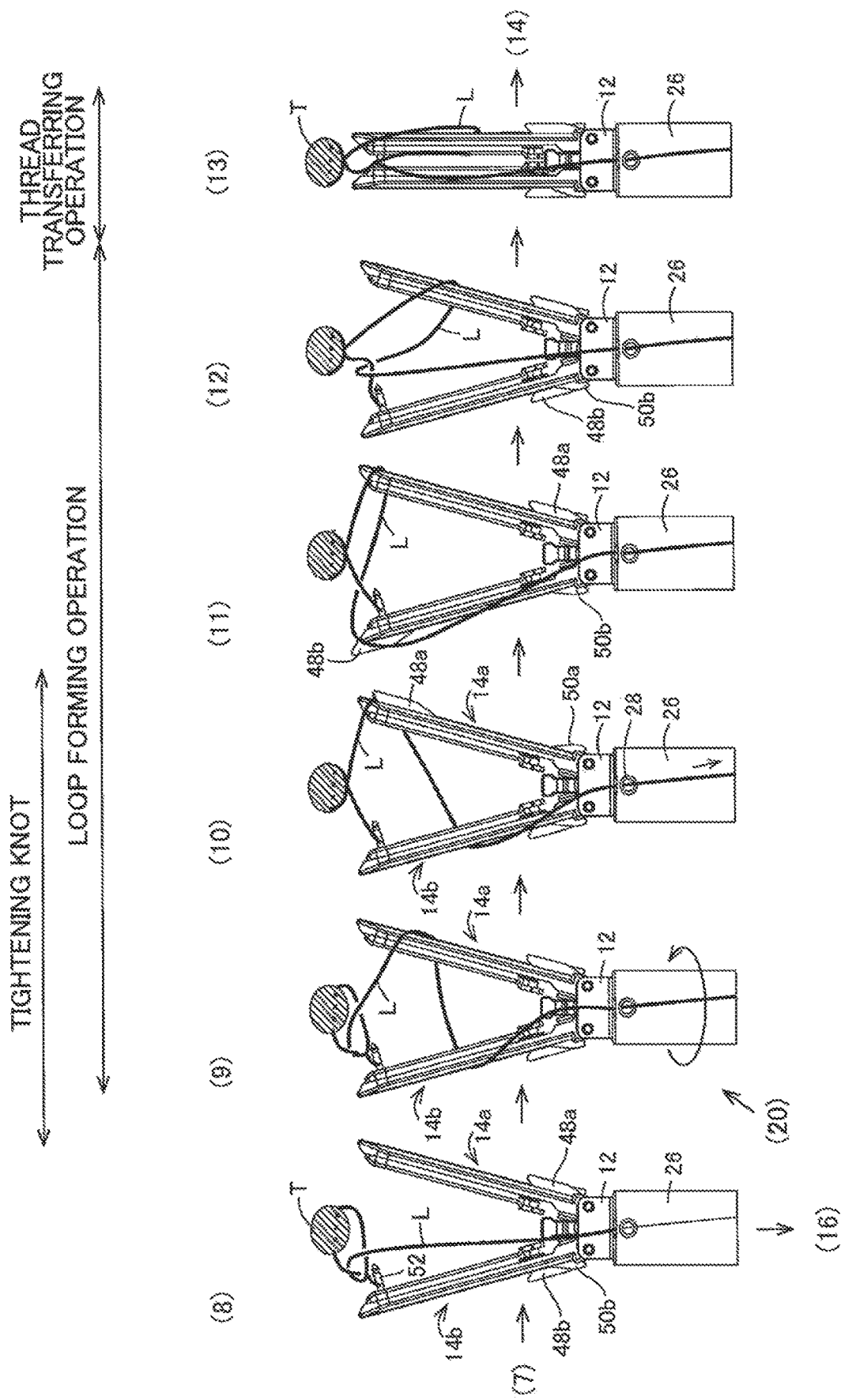
FIG. 14 is an explanatory diagram illustrating a part of steps in the knot forming operation performed subsequent to the steps illustrated in FIG. 13 by the knot forming device according to the first embodiment.

Next, steps (7) of FIG. 13 and (8) of FIG. 14 show the sequence of the loop moving operation. Specifically, by operating the linear operating member 20*a* to move the second movable member 48*b* of the second arm 14*b* from its proximal position to its distal position on the second aria 14*b*, as illustrated in (7) of FIG. 13, the thread-like member L wrapped around the second arm 14*b* is pushed off the distal end of the second arm 14*b* into the space between the second arm 14*b* and first arm 14*a*. Subsequently, the second movable member 48*b* is returned from the distal position to the proximal position on the second arm 14*b*, as, illustrated in (8) of FIG. 14. In this way, by transferring the needle 52 between the first arm 14*a* and second arm 14*b* while the first arm 14*a* and second arm 14*b* are closed, the portion the thread-like member L fixed to the needle 52 and constituting the first position is passed through the loop from the third position B side of the loop, which is the side farther from the first position with respect to the two intersecting positions of the thread-like member L corresponding to the intersecting point of the loop, to the second position A side, which is the side nearer the first position, and forms a knot M in the loop. In the present embodiment, the second arm 14*b* functions as the first loop retaining member that retains this loop.

When the knot formed in the thread-like member L is to be a knot in which the thread-like member L is closed in a loop surrounding the object being tied, the object being tied must be contained within the closed path formed of the thread-like member L, first arm 14*a*, second arm 14*b*, and elongate base member 12. For example, when the thread-like member L is used for suturing tissue T, the tissue T is placed between the distal ends of the first arm 14*a* and second arm 14*b* and the first arm 14*a* and second arm 14*b* are closed while the first end of the needle 52 is locked in the locking plate 40*a* of the first arm 14*a* so that the needle 52 passes through the portion of the tissue T to be sutured while the tissue T is interposed between the distal ends of the first arm 14*a* and second arm 14*b*. The first arm 14*a* and second arm 14*b* are subsequently opened while the second end of the needle 52 is locked in the locking plate 40*b* of the second arm 14*b*, at which time a portion of the tissue T is enclosed within the closed path formed by the thread-like member L, first arm 14*a*, second arm 14*b*, and elongate base member 12. Immediately after the first arm 14*a* and second arm 14*b* are opened, and specifically when the needle 52 passed through a prescribed position (i.e., the first position of the thread-like member L) is released by the locking plate 40*a* and locked by the locking plate 40*b*, the operating position of the rotary operating member 16 is near 225 degrees. This state is illustrated in (7) of FIG. 13 and (8) of FIG. 14.

Figure 15:
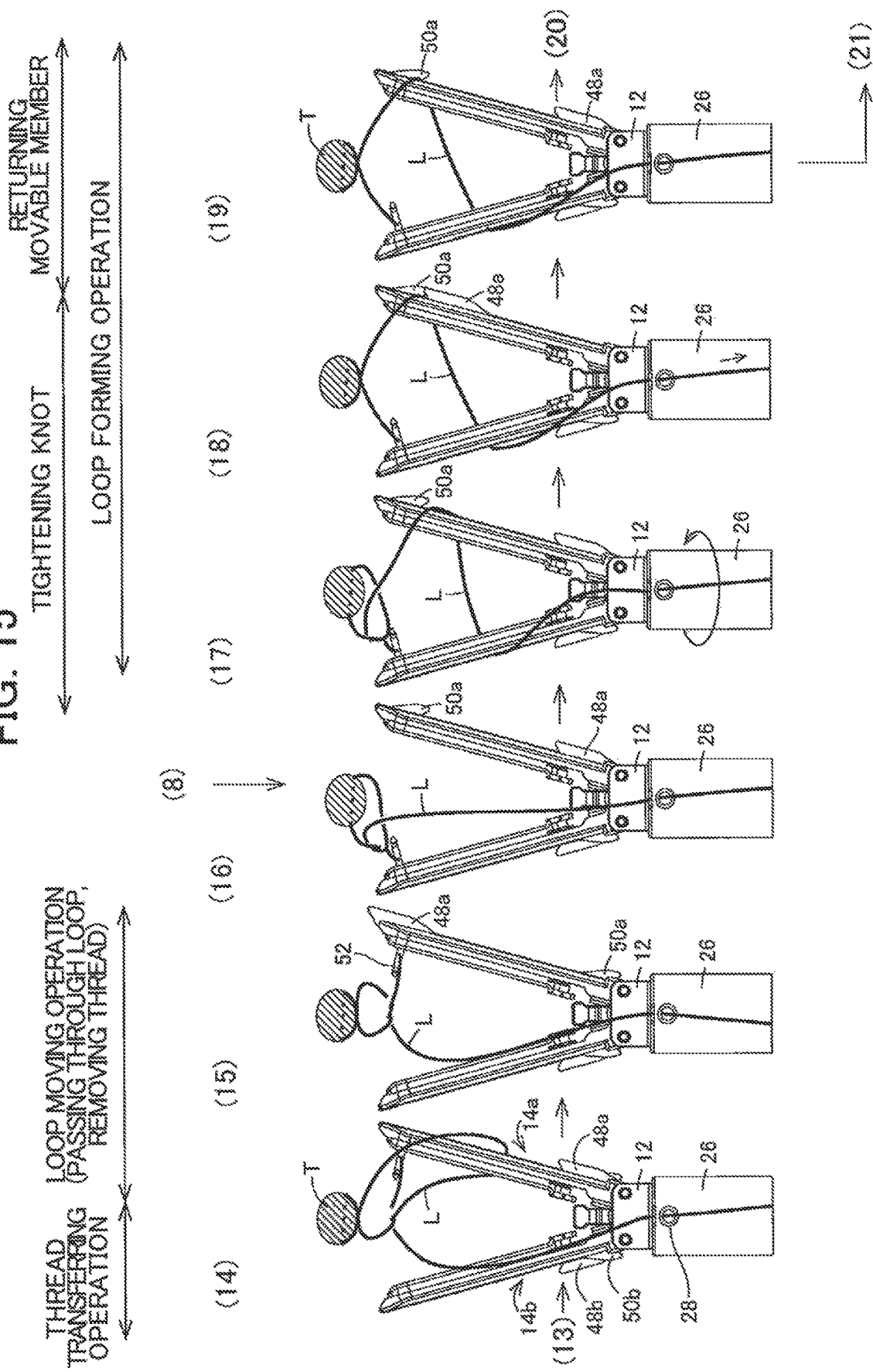
FIG. 15 is an explanatory diagram illustrating a part of steps in the knot forming operations performed subsequent to the steps illustrated in FIG. 14 by the knot forming device according to the first embodiment.
Figure 18:
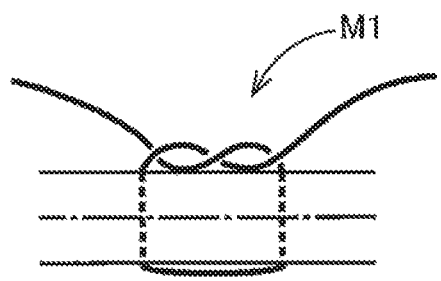
FIG. 18 is an explanatory diagram illustrating an overhand knot in the thread-like member formed through the knot forming operation shown in FIGS. 13 and 14.
Figure 19:
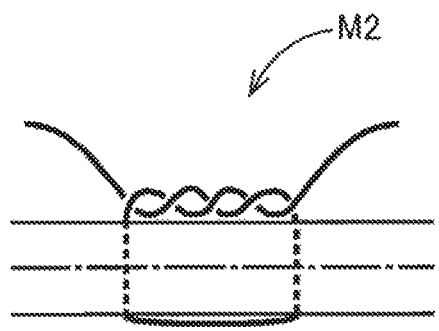
FIG. 19 is an explanatory diagram illustrating a double overhand knot in the thread-like member formed through the knot forming operation shown in FIGS. 13 and 14.

Steps (9) of FIG. 14 through (15) of FIG. 15 show example operations for tying the first knot, forming another loop, transferring the thread, moving the loop, and removing the thread that are performed after (8) of FIG. 14 in order to form a second knot. Steps (9) and (10) of FIG. 14 illustrate a tightening operation for the first knot. Specifically, by rotating the outer sleeve 26 one right-handed turn, as indicated in (9) of FIG. 14, the thread-like member L is wrapped around the outsides of the first arm 14*a* and second arm 14*b*. Next, by operating the linear operating member 18*a*, the first movable member 48*a* of the first arm 14*a* is moved from the proximal position to the distal position on the first arm 14*a*, as shown in (10) of FIG. 14, after which the thread-like member L is pulled at the fourth position, which is the portion of the thread-like member L passing through the thread guiding hole 28 to the rotary operating member 16 side, thereby tightening the knot. During this tightening operation, the thread-like member L on both sides of the tissue T form an angle of approximately 180 degrees and, thus, is approximately linear. The above steps form an overhand knot M1 shown in FIG. 18. Alternatively, the double overhand knot M2 shown in FIG. 19 is formed when the outer sleeve 26 is rotated two left-handed turns in (2) of FIG. 13.

Steps (11) and (12) in FIG. 14 illustrate a new loop forming operation. As shown in (11) of FIG. 14, the second movable member 48*b* of the second arm 14*b* is moved from its proximal position to its distal position relative to the second arm 14*b*, thereby removing the thread-like member L wrapped around the second arm 14*b* from the second arm 14*b*. Subsequently, the second movable member 48*b* is returned from the distal position to the proximal position, as shown in (12) of FIG. 14. When a second end or the fourth position of the thread-like member L is pulled in this state, the thread-like member L becomes wrapped around the first arm 14*a*, producing a loop in the thread-like member L around the first arm 14*a* for forming the second knot. Here, the first at 14*a* functions as the second loop retaining member that retains this loop. In this case, if a second path is the path from a second retaining position (i.e., a position at which the first position of the thread-like member L fixed to the needle 52 is retained by the second needle locking mechanism 24*b* of the second arm 14*b*) to the fourth position of the thread-like member L along the device body configured of the second arm 14*b* and elongate base member 12, this loop is formed around the second path. In other words, the first position of the thread-like member L is passed through the loop for forming the second knot from a sixth position side to a fifth position side, where the fifth position (third intersecting position) is the intersecting point of the loop between the first position and the fourth position (thread guiding hole 28) of the thread-like member L and the sixth position (fourth intersecting position) is the intersecting point positioned farther than the fifth position from the first position. The loop for forming the second knot described above is wrapped around the second path leading from the second retaining position of the second needle looking mechanism 24*b* provided on the second arm 14*b* to the fourth position of the thread-like member L along the second arm 14*b* and first arm 14*a* (device body). Further, the loop for forming this second knot intersects itself at the fifth position on the thread-like member L between the first and fourth positions and the sixth position that is farther than the fifth position from the first position, such that the sixth position is closer to the second retaining position than the fifth position along the second path.

Figure 20:
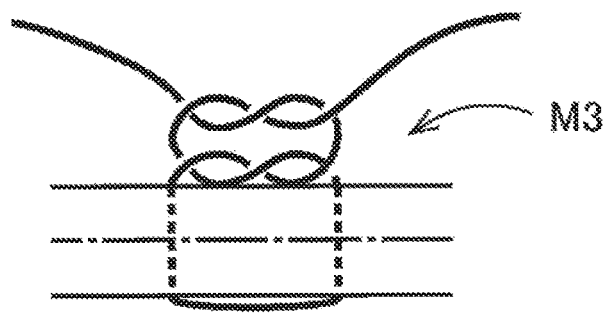
FIG. 20 is an explanatory diagram illustrating a granny knot in the thread-like member formed through the knot forming operation shown in FIGS. 13 through 16.
Figure 21:
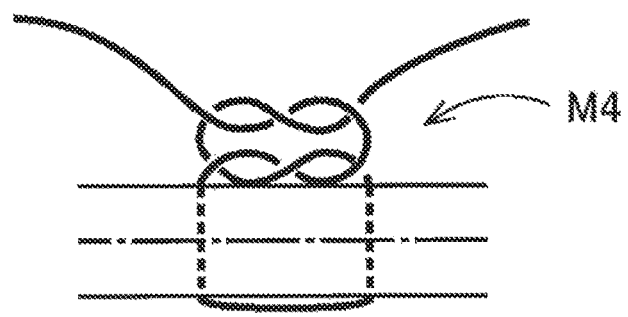
FIG. 21 is an explanatory diagram illustrating a square knot in the thread-like member formed through the knot forming operation shown in FIGS. 13 through 16.
Figure 22:
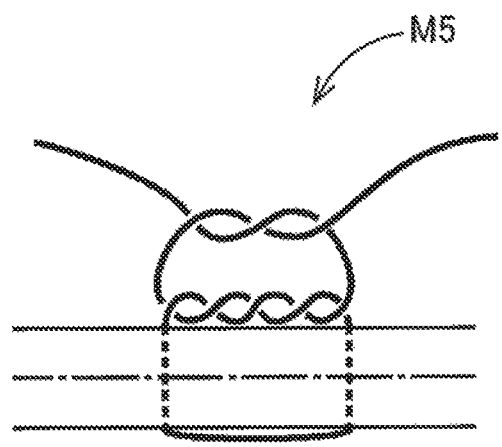
FIG. 22 is an explanatory diagram illustrating a surgeon's knot in the thread-like member formed through a double overhand knot forming operation and an overhand knot forming operation shown in FIGS. 13 through 16, where the surgeon's knot is formed by forming the overhand knot on the double overhand knot.

Steps (13) in FIG. 14 and (14) in FIG. 15 show the thread transferring operation, while step (15) in FIG. 15 shows the loop moving and thread removing operations. As shown in (13) of FIG. 14, the rotary operating member 16 is operated until its operating angle passes near 315 degrees, thereby closing the first arm 14a and second arm 14b without the tissue T interposed therebetween. At this time, the first end of the needle 52 is received in and locked by the first needle locking mechanism 24a of the first arm 14a and the second end of the needle 52 that was locked in the second needle locking mechanism 24b of the second arm 14b is released (unlocked). Next, the first arm 14a and second arm 14b are opened by rotating the rotary operating member 16 until its operating angle is either returned to 315 degrees or less or advanced to approximately 405 degrees. Step (14) of FIG. 15 shows this state. Next, the linear operating member 18a is operated for moving the first movable member 48a of the first arm 14a from its proximal position to its distal position on the first arm 14a, as shown in (15) of FIG. 15. At this time, the thread-like member L wrapped around the first arm 14a is pushed off the distal end of the first arm 14a into the area between the first arm 14a and second arm 14b. In other words, the needle 52 can be passed through the loop by removing the thread-like member L wrapped around the first arm 14a from the first arm 14a in (14) and (15) of FIG. 15. Next, the thread-like member L is pulled in order to tighten the second knot, forming a granny knot M3 shown in FIG. 20 through the simplest operations. Note that, the operation for retaining the thread-like member L near the distal end of the first arm 14a in order to perform an operation for tightening the thread-like member L is implemented by performing the operation in (8) through (10) of FIG. 14 with left and right directions reversed. However, since this is merely a repetition of the same operation, a description of this operation has been omitted. When forming a third knot, as when forming the second knot, this operation is performed in parallel with the third loop forming operation. Further, if the outer sleeve 26 is rotated one left-handed turn in the operation shown in (9) of FIG. 14, a square knot M4 shown in FIG. 21 is formed. On the other hand, if the double overhand knot M2 shown in FIG. 19 was formed in the first throw, a surgeon's knot M5 shown in FIG. 22 is formed.

However, since the thread-like member L is merely caught on the distal end of the first movable member 48a in the state shown in (10) of FIG. 14, if the tension in the thread-like member L not controlled at all times, the thread-like member L may come off the first movable member 48a. Steps (16) of FIG. 15 through (20) of FIG. 16 may be added between steps (8) and (9) of FIG. 14 as an example of an operation for more reliably preventing the thread-like member L from coming off when the thread-like member L is pulled to tighten the knot. Specifically, the linear operating member 20a is operated to move the third movable member 50a of the first arm 14a from its proximal position to its distal position on the first arm 14a, as shown in (16) of FIG. 15. Next, the outer sleeve 26 is rotated one right-handed turn to wrap the thread-like member L around the first arm 14a and second arm 14b, as shown in (17) of FIG. 15. Subsequently, the linear operating member 18a is operated to move the first movable member 48a of the first arm 14a from its proximal position to its distal position on the first arm 14a, as shown in (18) of FIG. 15, thereby interposing the thread-like member L wrapped around the first arm 14a between the third movable member 50a and first movable member 48a. In this state, the knot is tightened by performing an operation to pull the thread-like member L at the fourth position constituting the portion of the thread-like member L that has passed to the rotary operating member 16 side through the thread guiding hole 28. This portion of the thread-like member L interposed between the third movable member 50a and first movable member 48a corresponds to the seventh position in the present disclosure. The portion of the thread-like member L interposed between the fourth movable member 50b and the second movable member 48b corresponds to the eighth position in the disclosure. Next, the linear operating member 18a is operated to move the first movable member 48a of the first arm 14a from its distal position to its proximal position on the first arm 14a, as shown in (19) of FIG. 15. As shown in (20) of FIG. 16, the outer sleeve 26 is then rotated one left-handed turn (i.e., the direction opposite the rotation in (17) of FIG. 15) thereby unwrapping the thread-like member L that was wrapped around the first arm 14a and second arm 14b. While not shown in the drawings, the linear operating member 20a is also operated at the same time to move the third movable member 50a of the first arm 14a from its distal position to its proximal position on the first air 14a. The series of operations described above can reliably tighten the knot and remove the thread-like member L from the first arm 14a. After completing (20) in FIG. 16, the granny knot M3 is formed by executing the operation indicated in (9) through (13) of FIG. 14 and (14) and (15) of FIG. 15 described above. Further, the square knot M4 can be formed by rotating the outer sleeve 26 one left-banded turn in the operation shown in (9) of FIG. 14. High reliability can be ensured when forming a knot in the operation of (1) of FIG. 13 through (8) of FIG. 14, (16) through (20) of FIG. 15, (9) of FIG. 14 through (15) of FIG. 15, and (19) of FIG. 15 through (20) of FIG. 16, since tightening the thread-like member L is performed while the seventh position of the thread-like member L is interposed between the first movable member 48a and third movable member 50a.

Figure 16:
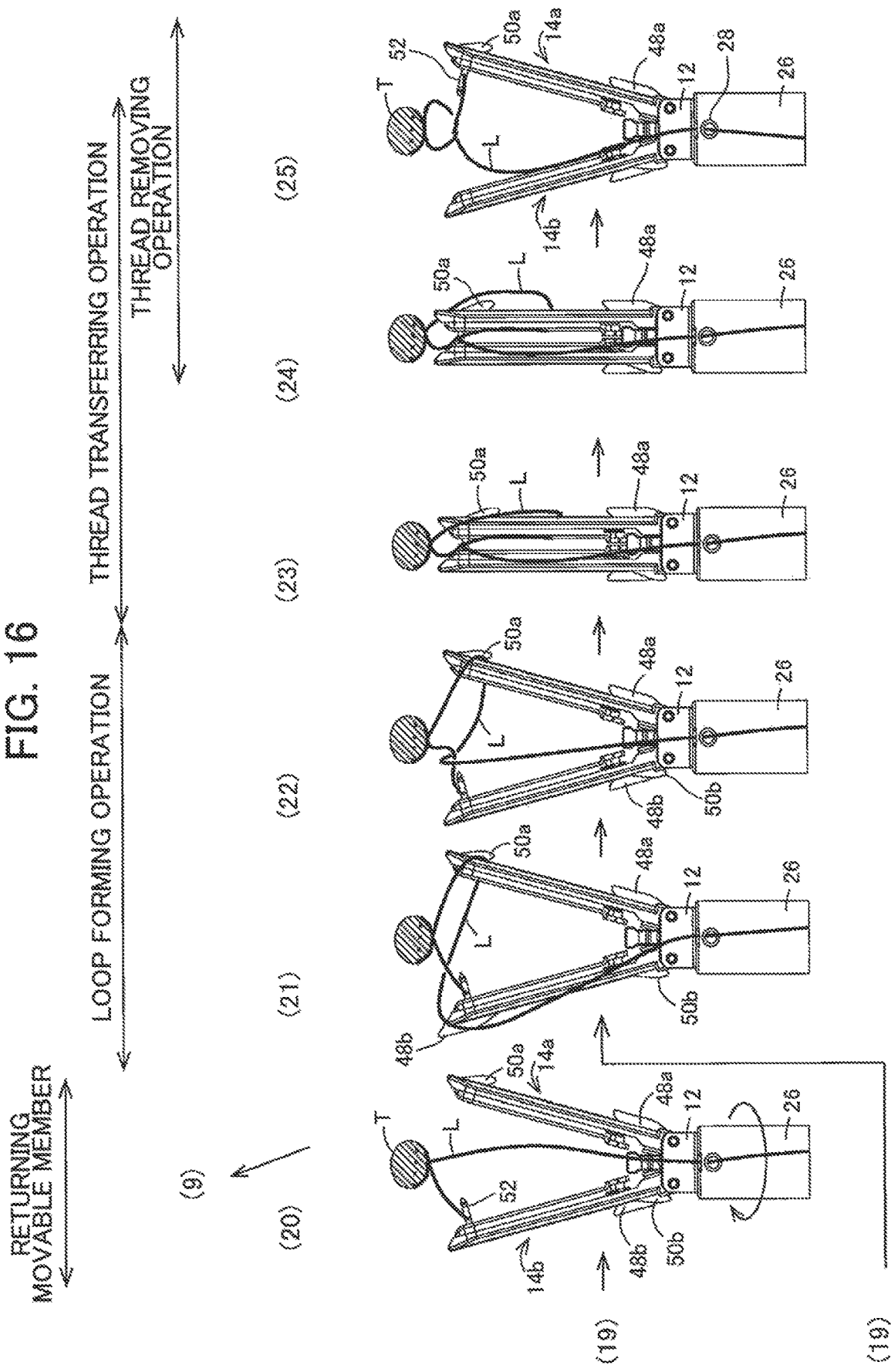
FIG. 16 is an explanatory diagram illustrating a part of steps in the knot forming operations performed subsequent to the steps illustrated in FIG. 15 by the knot forming device according to the first embodiment.

Steps (21) through (25) of FIG. 16 show a variation of the procedure described above as an example of loop forming, thread transferring, and thread removing operations for forming the second knot after (19) of FIG. 15. This variation improves the inefficiency of the procedure described above whereby the loop formed in (17) of FIG. 15 is unwrapped in (20) of FIG. 16. Steps (21) and (22) of FIG. 16 show the loop forming operation. As shown in (21) of FIG. 16, the linear operating member 18b is operated to move the second movable member 48b of the second arm 14b from the proximal position to the distal position on the second arm 14b. Through this operation, the thread-like member L wrapped around the second arm 14b is pushed between the second arm 14h and first arm 14a, as shown in (22) of FIG. 16.

Step (23) of FIG. 16 shows the thread transferring operation, and steps (24) and (25) of FIG. 16 show the thread removing operation. As shown in (23) of FIG. 16, by rotating the rotary operating member 16 until its operating angle passes near 315 degrees, the first arm 14a and second arm 14b are closed without the tissue T interposed therebetween, and the first end of the needle 52 is received in and locked by the first needle locking mechanism 74a of the first arm 14a, while the second end that was locked in the second needle locking mechanism 24b of the second arm 14b is released (unlocked). Next, the knot forming device 10 is withdrawn a prescribed distance toward the proximal side, then subsequently advanced back toward the distal side, causing the thread-like member L positioned in front of the distal end of the first arm 14*a* in the perspective of the drawing to move behind the distal end of the first arm 14*a* in the drawing, as shown in (24) of FIG. 16, thereby removing the thread-like member L from the distal end of the first arm 14*a*. Subsequently, the first arm 14*a* and second arm 14*b* are opened by rotating the rotary operating member 16 to return its operating angle to 315 degrees or less or by rotating the rotary operating member 16 until its operating angle passes near 405 degrees. Step (25) of FIG. 16 shows the resulting state. By pulling the second end or the fourth position of the thread-like member L in this state, the second knot is tightened to form the granny knot M3 shown in FIG. 20 through the simplest operations. Alternatively, if the outer sleeve 26 was rotated one left-handed turn in the operation shown in (17) of FIG. 15, the square knot M4 shown in FIG. 21 will be formed. On the other hand, if the double overhand knot M2 shown in FIG. 19 was formed as the first throw, the surgeon's knot M5 shown in FIG. 22 will be formed. This variation is more efficient when forming a knot in the operations of (1) through (8) of FIG. 13, (16) through (19) of FIG. 15, and (21) through (25) of FIG. 16 since the loop formed in (17) of FIG. 15 is not subsequently unwrapped in (20) of FIG. 16.

When forming a multi-throw knot that combines the knots from a plurality of throws, as in the above description, operations are first performed to form a knot of a prescribed throw, such as the first throw, and subsequently to form a separate knot following the knot in the first throw. In this operation, the second arm 14*b* holds the needle 52 in the present embodiment until the first throw has been formed. Therefore, the knot in the second throw can be formed by repeating the transferring operation for the needle 52, maiming the device to its initial state, and performing the same operation again. Since the first arm 14*a* and second arm 14*b* are symmetrically constructed in the present embodiment, the second knot can be formed immediately following formation of the first knot. The present embodiment describes an example in which a knot is formed in two throws. However, when forming a knot in three or more throws, the components used in the operations for odd-numbered throws are identical to those used in the first throw of the present embodiment. The components used in operations for even-numbered throws are determined by reading the procedure for forming knots in odd-numbered throws while exchanging the appended "a" and "b" in the first arm 14*a* and second arm 14*b* and their components.

Further, while the knot forming operation described above involves individual steps performed in series for simplifying the description, the following steps can be performed simultaneously: (6) and (7) of FIG. 13, (8) and (9) of FIG. 14, (10) and (11) of FIG. 14, (12) and (13) of FIG. 14, (14) and (15) of FIG. 15, (8) of FIG. 14 and (16) of FIG. 15, (19) of FIG. 15 and (20) of FIG. 16, and (19) of FIG. 15 and (21) of FIG. 16.

According to the knot forming device 10 of the present embodiment, the operations of the first movable member 48*a*, second movable member 48*b*, first needle looking mechanism 24*a*, and second needle locking mechanism 24*b* move the loop formed in the thread-like member L (tying medium), which is retained by the second arm 14*b* (i.e., the first loop retaining member), and switch the relative positional relationship between the loop and the first position of the thread-like member L in the first path. These operations can automatically generate a knot by forming an enclosed loop between the second position (first intersecting position) A and third position (second intersecting position) B of the thread-like member L.

According to the knot forming device 10 of the present embodiment, the second arm 14*b* can perform a contacting/separating operation relative to the first arm 14*a* along a direction orthogonal to the elongated direction (first direction) of the elongate base member (base part) 12, tied the rotary operating member 16 and linear operating members 18*a*, 20*a*, 18*b*, and 20*b* (operating parts) can also perform operations for bringing together and separating the first arm 14*a* and second arm 14*b*. By bringing together and separating the first arm 14*a* and second arm 14*b*, the rotary operating member 16 moves the loop formed in the thread-like member L retained on the second arm 14*b* (i.e., the first loop retaining member) relative to the first position of the thread-like member L retained by the first retaining member of the first needle locking mechanism 24*a* and can switch the relative positions of the loop, and first position along the first path.

According to the knot forming device 10 of the present embodiment, the rotary operating member 16 and the linear operating members 18*a*, 20*a*, 18*b*, and 20*b* (operating parts) sequentially execute a first moving operation for bringing together, or closing, the first arm 14*a* and second arm 14*b* (third orientation); a switching operation for switching the retained state of the first position of the thread-like member L from a state retained by the first retaining member of the first arm 14*a* to a state retained by the second retaining member of the second arm 14*b*; a second moving operation for separating the first arm 14*a* and second arm 14*b* from each other to open the same (second orientation) from the state in which the first arm 14*a* and second arm 14*b* are relatively near each other (third orientation); and a loop moving operation for controlling the first moving portion (second movable member 48*b*) to move the loop formed in the thread-like member L along the first path in a direction toward the second retaining member of the second arm 14*b*. Since the first moving operation, second moving operation, and loop moving operation are implemented by operating the rotary operating member 16, the above operations can automatically generate a knot by forming an enclosed loop between the second position (first intersecting position) A and third position (second intersecting position) B of the thread-like member L.

According to the knot forming device 10 of the present embodiment, the thread-like member L is wrapped around a second path extending from the second retaining position of the second retaining member provided on the second arm 14*b* to the fourth position of the thread-like member L. The knot forming device 10 further includes a second loop retaining member (the first arm 14*a*) for retaining the loop formed in the thread-like member L wherein a fifth position (first intersecting position) between the first position and fourth position of the thread-like member L intersects a sixth position (fourth intersecting position) farther than the fifth position from the first position such that the sixth position is closer than the fifth position to the second retaining position along the second path; and a second moving portion (first movable member 48*a*) that moves the loop formed in the thread-like member L retained by the second loop retaining member relative to the first position of the thread-like member L retained by the second retaining member and changes the relative positions of the loop and the first position along the second path. Further, the rotary operating member 16 and the linear operating members 18*a*, 20*a*, 18*b*, and 20*b* (operating parts) also operate the second moving portion (first movable member 48*a*). Accordingly, the operating parts operate the second moving portion (first movable member 48*a*) for moving the loop formed in the thread-like member L retained by the second loop retaining member (first arm 14*a*) relative to the first position retained by the second retaining member disposed on the second arm 14*b* and change the relative positions of the loop and first position along the second path.

According to the knot forming device 10 of the present embodiment, the rotary operating member 16 and the linear operating members 18*a*, 20*a*, 18*b*, and 20*b* (operating parts) form a knot by controlling the first moving portion (second movable member 48*b*) to shift the orientation of the thread-like member L from a first state (first orientation) in which the first position of the thread-like member L is retained by the first retaining member disposed on the first arm 14*a* and is separated from the second retaining member disposed on the second arm 14*b*, and the loop nearest the first position is retained by the first loop retaining member (second arm 14*a*) through a third state (third orientation) in which the first position contacts both the first retaining member and second retaining member to a second state (second orientation) in which the first position is retained by the second retaining member disposed on the second arm 14*b* and separated from the first retaining member disposed on the first arm 14*a*. By actuating the first to portion (second movable member 48*b*), these operating parts form a knot by changing the orientation from the first state in which the loop nearest the first position is retained by the first loop retaining member (second arm 14*b*) to the second state via the third state.

According to the knot forming device 10 of the present embodiment, the loop retained by the first loop retaining member (second arm 14*b*) and the loop retained by the second loop retaining member (first arm 14*a*) are wrapped around the ring-like third path in a direction opposite the loop used to form the knot of the first throw, where the third path extends from the elongate base member 12 (base part) past the device body (second arm 14*b*), through the second retaining member provided on the second arm 14*b* and the first retaining member provided on the first arm 14*a*, past the device body (first arm 14*a*), to the elongate base member 12 (base part). In this way, when performing multiple throws for forming a knot in an operation from the state in which the first position of the thread-like member L is retained by the first retaining member disposed on the first arm 14*a* and is separated from the second retaining member disposed on the second arm 14*b* (first orientation) to the state in which the first position is retained by the second retaining member and separated from the first retaining member (second orientation), the knot forming device 10 can form through multiple throws a square knot M4 that is unlikely to come untied, by reversing the orientation of the loops used in the first throw and second throw.

According to the knot forming device 10 of the present embodiment, the loop retained by the first loop retaining member (second arm 14*b*) and the loop retained by the second loop retaining member (first arm 14*a*) are wrapped around the ring-like third path in the same direction a the loop for forming a knot in the first throw, where the third path extends from the elongate base member 12 (base part) past the device body (second arm 14*b*) via the second retaining member disposed on the second arm 14*b* and the first retaining member disposed on the first arm 14*a*, past the device body (first arm 14*a*), to the elongate base member 12 (base part). In this way, when performing multiple throws to form a knot in an operation from the state in which the first position of the thread-like member L is retained by the first retaining member disposed on the first arm 14*a* and separated from the second retaining member disposed on the second arm 14*b* (first orientation) to the state in which the first position is retained by the second retaining member and separated from the first retaining member (second orientation), the knot forming device 10 can form the granny knot M3, which is a multi-throw knot that tightens easily, by using loops with the same orientation in the first and second throws.

According to the knot forming device 10 of the present embodiment, the first loop retaining member (the second arm 14*b*) retains a loop that is wrapped once around the first path extending from the first retaining position of the first retaining member provided on the first arm 14*a* along the device body (first arm 14*a*, the elongate base member 12, and the second arm 14*b*) to the fourth position on the second end side of the thread-like member L. In this way, the knot forming device 10 can form the overhand knot M1, which is the most basic knot.

According to the knot forming device 10 of the present embodiment, the first loop retaining member (the second arm 14*b*) retains a loop wrapped twice around the first path. In this way, the knot forming device 10 can form the double overhand knot M2, which is the next simplest knot after the overhand knot M1 and has better binding strength than the overhand knot M1.

According to the knot forming device 10 of the present embodiment the first loop retaining member (second arm 14*b*) retains a loop wrapped twice around the first path, and the second loop retaining member (first arm 14*a*) retains a loop wrapped once around the second path. In this way, the knot forming device 10 can form the surgeon's knot M5 comprising a doable overhand knot in the first throw and a simple overhand knot in the second throw.

The knot forming device 10 of the present embodiment has the outer sleeve 26 and the first movable member 48*a* (loop forming member and first loop forming member) for forming a loop in the thread-like member L that intersects at the second position (first intersecting position) A kind the third position (second intersecting position) B such that the third position B is closer than the second position A to the first retaining position along the first path and for retaining the loop on the second arm 14*b* (first loop retaining member). These operations eliminate the need to set the loop on the second arm 14*b* (first loop retaining member) in advance, thereby reducing the time and effort required for preparation.

The not forming device 10 according to the present embodiment has the outer sleeve 26 and second movable member 48*b* (loop forming member and second loop forming member) for forming a loop in the thread-like member L that intersects at the fifth position (third intersecting position) and sixth position (fourth intersecting position) such that the sixth position is closer than the fifth position to the second retaining position along the second path, and for retaining this loop on the first arm 14*a*. In this way, after thrilling a knot in a loop retained on the second arm 14*b* (first loop retaining member), the knot forming device 10 can form the next loop without transferring the first position of the thread-like member L. Further, after forming a knot in a loop retained on the first arm 14*a* (second loop retaining member), the knot forming device 10 can form the next knot without transferring the first position of the thread-like member L. In other words, the knot forming device 10 can tie knots in an arbitrary number of throws, without being limited to a preset number of knots.

According to the knot forming device 10 of the present embodiment, the first loop retaining member (second arm 14b) retains the thread-like member L when the thread-like member L is wrapped around the portion of the second arm 14b between the elongate base member 12 and the second retaining member along the first path of the second arm 14b. The loop forming member (the outer sleeve 26 and first movable member 48a) has the outer sleeve (rotating member) 26 that rotates the fourth position of the thread-like member L relative to the first arm 14a and second arm 14b to wrap the thread-like member L around the central axis C1 cape elongate base member (base part) 12 extending in the longitudinal direction; and the first movable member (third moving portion) 48a that moves the thread-like member L wrapped around the central axis C1 along the first path relative to the first retaining position. Through these operations, the thread-like member L is wrapped around the first path extending from the first retaining position to the fourth position on the thread-like member L along the first arm 14a (the device body). Thus, the knot forming device 10 can wrap the thread-like member L mound the second arm 14b to easily form a loop in advance by arranging the second position (first intersecting position) A between the first position and fourth position of the thread-like member L to intersect the third position (second intersecting position) B that is farther than the second position A from the first position, such that the third position B is closer than the second position A on the first path to the first retaining position of the first retaining member provided on the first arm 14a. This arrangement can also give the second arm 14b itself the function of a loop retaining member, thereby simplifying the knot forming device 10.

According to the knot forming device 10 of the present embodiment, the above-described third moving portion (first movable member 48a) is the second moving portion (first movable member 48a). In this way, the same thread removing mechanism can be used for forming the loop and for forming a knot after transferring the end of the thread-like member L, thereby simplifying the knot forming device 10.

According to the knot forming device 10 of the present embodiment, the first arm 14a (second loop retaining member) retains the thread-like member L when the thread-like member L is wrapped around the portion of the first arm 14a between the elongate base member 12 and the first retaining member provided on the first arm 14a along the second path of the first arm 14a. The loop forming member (the outer sleeve 26 and second movable member 48b) has the outer sleeve (rotating member) 26 that rotates the fourth position of the thread-like member L relative to the first arm 14a and second arm 14b to wrap the thread-like member L around the central axis C1 of the elongate base member (base part) 12 extending in the longitudinal direction; and the second movable member (third moving portion) 48b that moves the thread-like member L wrapped around the central axis C1 along the second path relative to the second retaining position retained by the second retaining member disposed on the second arm 14b. Through these operations, the thread-like member L is wrapped around the second path extending from the second retaining position of the second retaining member disposed on the second arm 14b to the fourth position on the thread-like member L along the second arm 14b (the device body). Thus, the knot forming device 10 can wrap the thread-like member L around the first arm 14a to easily form a loop in advance by arranging the fifth position (third intersecting position) between the first position and fourth position of the thread-like member L to intersect the sixth position (fourth intersecting position) that is farther than the fifth position from the first position, such that the sixth position is closer than the fifth position on the second path to the second retaining position. This arrangement can also give the first arm 14a itself the function of loop retaining member, thereby simplifying the knot forming device 10.

According to the knot forming device 10 of the present embodiment, the above-described third moving portion (second movable member 48b) is the first moving portion (second movable member 48b). In this way, the same thread removing mechanism can be used for forming the loop and for forming a knot after transferring the end of the thread-like member L, thereby simplifying the knot forming device 10.

According to the knot forming device 10 of the present embodiment, the second movable member 48b (first moving portion) moves the thread-like member L along the first path in a direction away from the elongate base member 12 (base part). By moving the second movable member 48b (first moving portion) in a direction away from the elongate base member 12 (base part) along the first path, this configuration can move the loop so that the first position moves relative to the loop and passes therethrough.

According to the knot forming device 10 of the present embodiment, the first movable member 48a (second moving portion) moves the thread-like member L along the second path in a direction away from the elongate base member 12 (base part). Since the first movable member 48a (second moving portion) moves the thread-like member L in a direction away from the base part along the second path, this operation can move the loop so that the first position moves relative to the loop and passes therethrough.

According to the knot forming device 10 of the present embodiment, the first position of the thread-like member L is alternately retained by the first retaining member disposed on the first arm 14a and the second retaining member disposed on the second arm 14b via the needle 52 (needle-like member) having sufficient hardness and a sharp pointed shape. Thus, if the needle 52 (needle-like member) is placed on the end of the thread-like member L, when the end of the thread-like member L is transferred through a state (third orientation) in which the first position contacts both the first retaining member provided on the first arm 14a and the second retaining member provided on the second arm 14b, the first position can be transferred by passing the needle 52 (needle-like member) through the tissue T (object being tied) while the tissue T is interposed between the first at 14a and second arm 14b, thereby providing a knot forming device 10 having three functions: suturing, tying, and tightening.

The knot forming device 10 according to the present embodiment is also provided with the first movable member 48a and third movable member 50a (first guide members) disposed on the rear surface of the first arm 14a for supporting the seventh position of the thread-like member L, and the second movable member 48b and fourth movable member 50b (second guide members) disposed on the rear surface of the second arm 14b for supporting the eighth position of the thread-like member L. The first movable member 48a (first guide member) can move the thread-like member L along the first path in a direction away from the elongate base member 12 (base part), and supports the seventh position of the thread-like member L while restraining movement of the seventh position at a position separated from the elongate base member 12 (base part) by at least a first distance. The second movable member 48b (second guide member) can move the thread-like member L along the second path in a direction away from the elongate base member 12 (base part), and supports the eighth position of the thread-like member L while restraining movement of the eighth position at a position separated from the elongate base member 12 (base part) by at least the first distance. With this configuration, when the third movable member 50a or fourth movable member 50b (first and second guide members) is positioned nearer to the distal end of the corresponding first arm 14a and second arm 14b while performing an operation to tighten the knot, the thread-like member L can be palled in a state where the three members that include the first retaining member disposed on the first arm 14a, the knot formed in the tissue T (object being tied), and second retaining member disposed on the second arm 14b are arranged in a line, i.e., at an angle near 180 degrees the knot in the middle. Through this operation, the knot forming device 10 can form a knot that securely closes the tissue T (object being tied).

According to the knot forming device 10 of the present embodiment, the third movable member 50a and fourth movable member 50b (first and second guide members) can move the thread-like member L along the first path and second path, respectively, in a direction approaching the elongate base member 12 (base part). The third movable member 50a (first guide member) supports the seventh position of the thread-like member L and restrains movement of this seventh position at a position separated from the elongate base member 12 (base part) no more than a second distance longer than the first distance, whereas the fourth movable member 50b (second guide member) supports the eighth position of the thread-like member L and restrains movement of this eighth position at a position separated from the elongate base member 12 (base part) no more than the second distance. In this way, when performing an operation to tighten a knot by pulling the thread-like member L while all three of the first retaining member provided on the first arm 14a, the knot formed in the tissue T (object being tied), and the second retaining member provided on the second arm 14b are arranged in a line, the distance between the first arm 14a and second arm 14b can be reduced, making the knot forming device 10 more compact.

According to the knot forming device 10 of the present embodiment, the first position of the thread-like member L is alternately retained by the first retaining member disposed on the first arm 14a and the second retaining member disposed on the second arm 14b via the needle 52 (needle-like member) having sufficient hardness and a sharp pointed shape. Both ends of the needle 52 are formed in a sharp point, including a first end retained M the first retaining member and a second end retained in the second retaining member. Consequently, the needle 52 can be passed through the tissue T in operations performed M both directions between the first arm 14a and second at 14b. Accordingly, the knot forming device 10 can implement various methods of use to suit the application, such as performing a plurality of sutures, or performing operations in the sequence suture, knot, suture.

According, to the knot forming device 10 of the present embodiment, the needle 52 (needle-like member) has the engaging grooves 53 and 54 (V-shaped grooves) respectively formed in the first end retained by the first retaining member provided on the first arm 14a and the second end retained by the second retaining member provided on the second arm 14b. The first retaining member and second retaining member retain the needle 52 through the locking plates 40a and 40b (locking members) and are selectively inserted into the V-shaped engaging grooves 53 and 54. In this way, the needle-like member is reliably retained in the first retaining member disposed on the first arm 14a and the second retaining member disposed on the second arm 14b.

According to the knot forming device 10 of the present embodiment, the first guide member (first movable member 48a) has a guide surface (sloped receiving surface 66a) provided on the side farther from the elongate base member 12 (base part). With this arrangement, the first guide member (first movable member 48a) supports the seventh position of the thread-like member L from the elongate base member 12 (base part) side, and can easily move the thread-like member L along the first path. Hence, the knot forming device 10 can be simplified and made more compact.

According to the knot forming device 10 of the present embodiment, the first guide member functions as the first movable member 48a. Accordingly, the first guide member that supports the seventh position of the thread-like member L also serves as the second moving portion that moves the loop formed in the thread-like member L and retained by the first arm 14a (second loop retaining member) relative to the first position of the thread-like member L retained by the second retaining member disposed on the second arm 14b, and changes the relative positions of the loop and the first position along the second path. Hence, the knot forming device 10 can be simplified and made more compact.

According to the knot forming device 10 of the present embodiment, the second guide member (second movable member 48b) has a guide surface (sloped receiving surface 66b) provided on the side farther from the elongate base member 12 (base part). With this arrangement, the second guide member (second movable member 48b) supports the eighth position of the thread-like member L from the elongate base member 12 (base part) side, and can, easily move the thread-like member L along the second path. Hence, the knot forming device 10 can be simplified and made more compact.

According to the knot forming device 10 of the present embodiment, the second guide member functions as the second movable member 48b. Accordingly, the second guide member that supports the eighth position of the thread-like member L also moves the first moving portion that moves the loop formed in the thread-like member L and retained by the second arm 14b (first loop retaining member) relative to the first position of the thread-like member L retained by the first retaining member disposed on the first arm 14b, and changes the relative positions of the loop and the first position along the first path. Hence, the knot forming device 10 can be simplified and made more compact.

Second Embodiment

Next, a second embodiment of the present disclosure will be described. In the following description, like parts and components are designated with the same reference numerals to avoid duplicating description.

Figure 23:
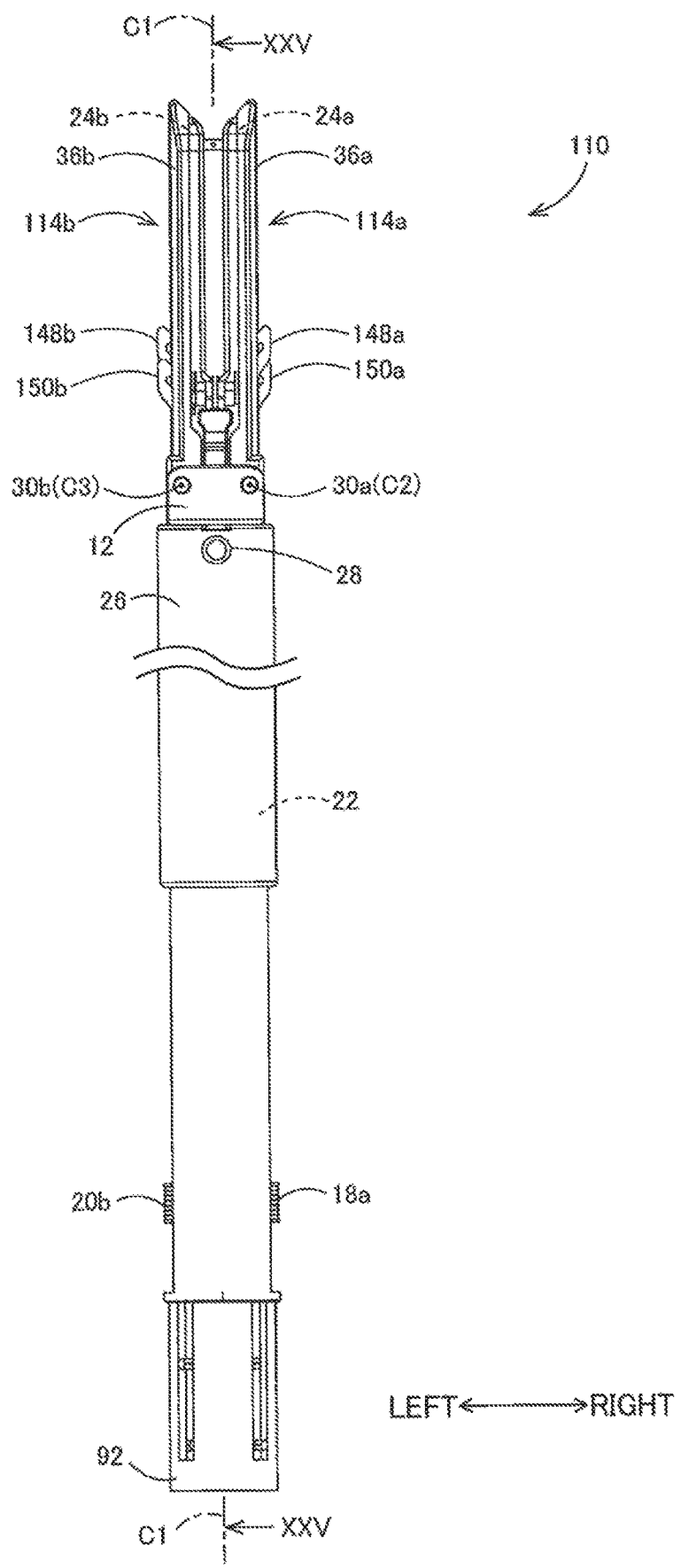
FIG. 23 is a front view showing a knot forming device according to a second embodiment of the present disclosure when a first arm and a second arm are in a closed state, from which a rotary operating member is omitted.
Figure 24:
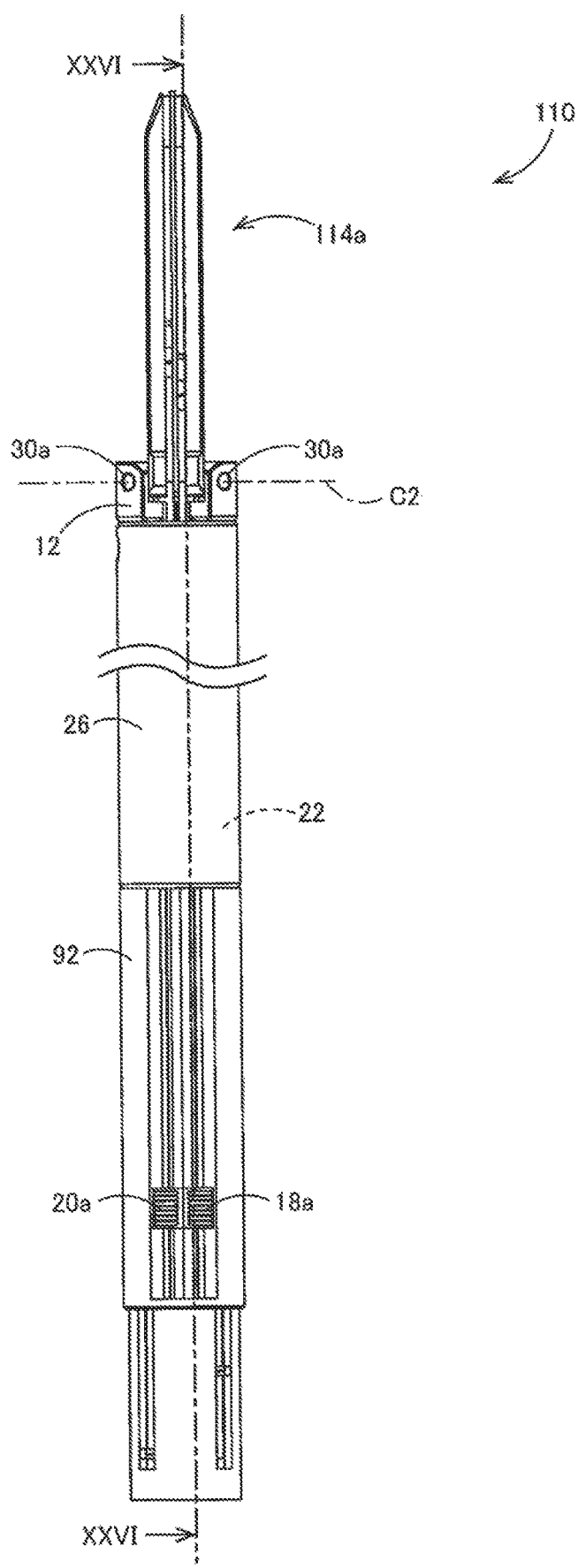
FIG. 24 is a fight side view showing the knot forming device when the first arm and the second arm are in the closed state in the second embodiment.
Figure 25:
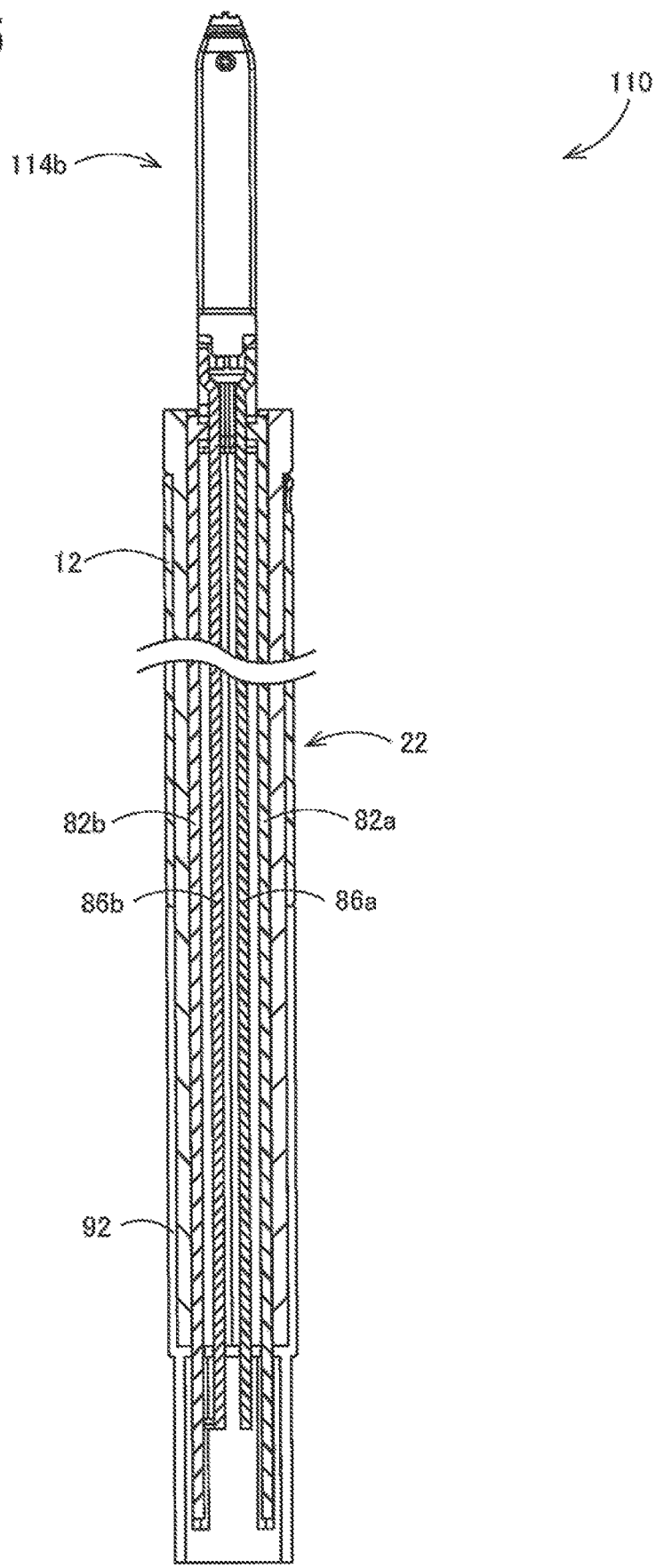
FIG. 25 is a vertical cross-sectional view of the knot forming device taken along a plane XXV-XXV of FIG. 23 in the second embodiment.
Figure 26:
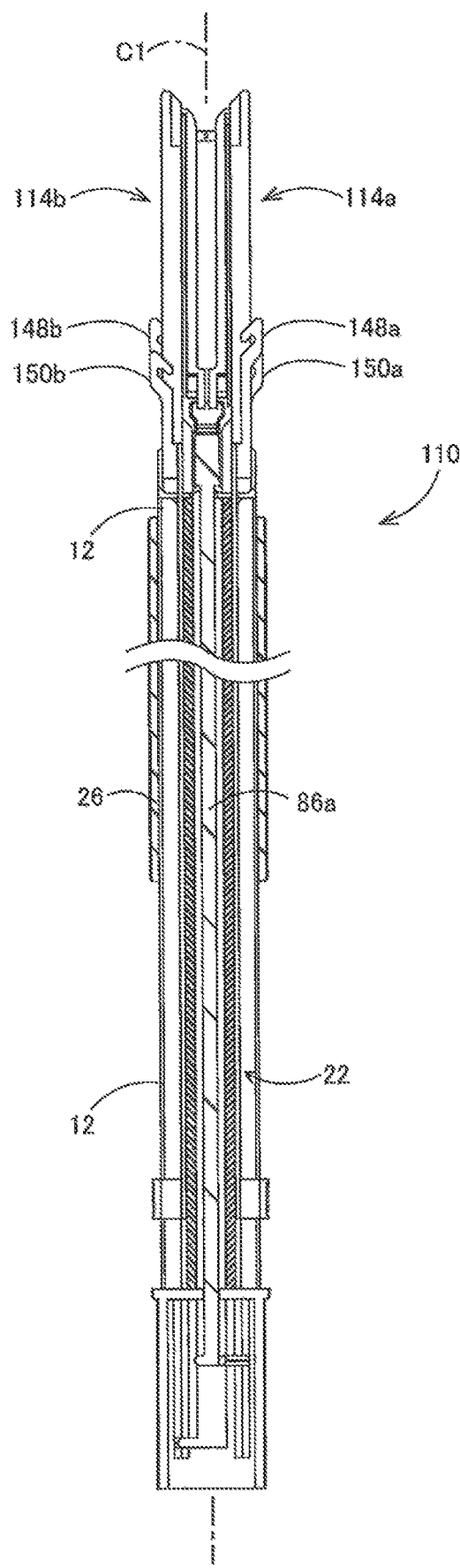
FIG. 26 is a vertical cross-sectional view of the knot forming device taken along a plane XXVI-XXVI of FIG. 24 in the second embodiment.
Figure 27:
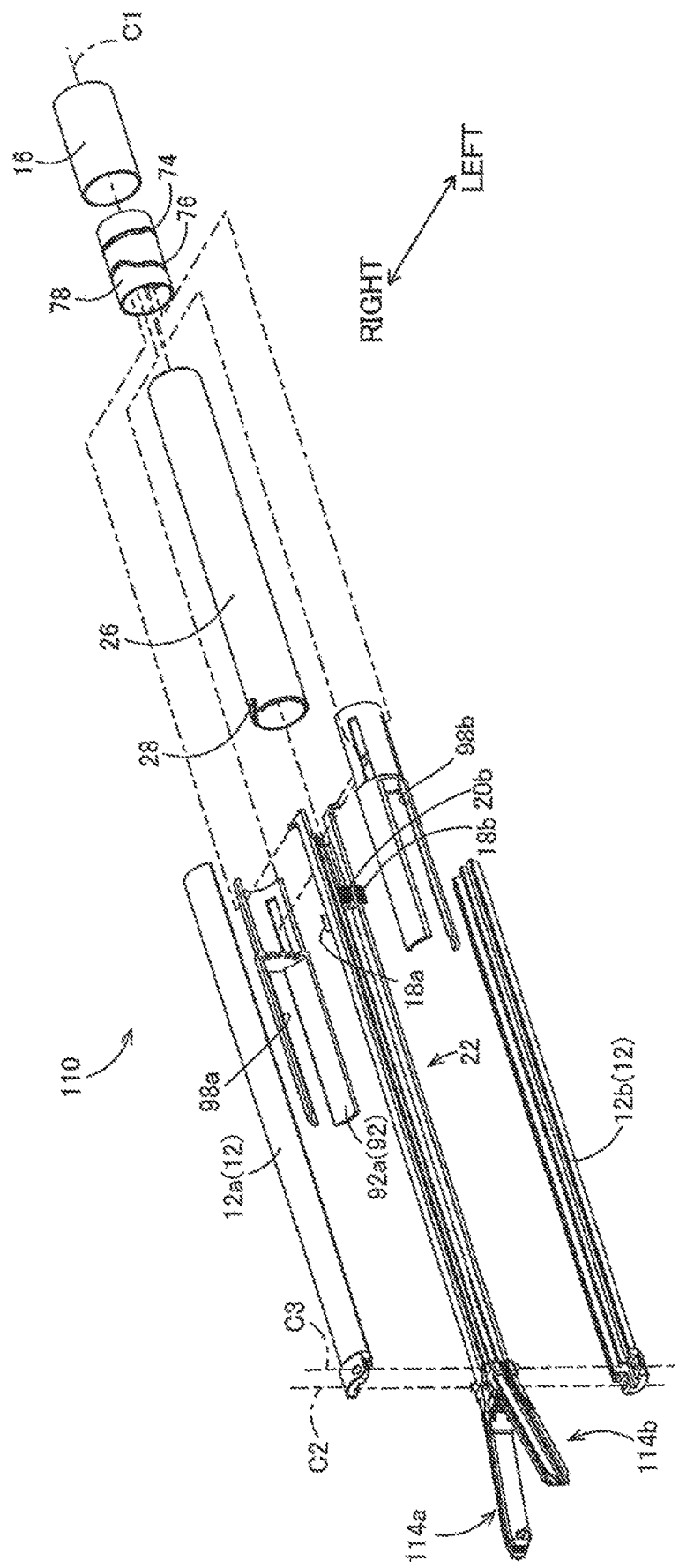
FIG. 27 is an exploded perspective view illustrating a structure of the knot forming device according to the second embodiment.

FIG. 23 is a front view showing a knot forming device 110 according to the second embodiment when a first arm 114a and a second arm 114b are in a closed state. FIG. 24 is a right side view showing the knot forming device 110 when the first arm 114a and second arm 114b are in the closed state. FIG. 25 is a cross-sectional view taken along the plane XXV-XXV in FIG. 23. FIG. 26 is a cross-sectional view taken along the plane XXVI-XXVI in FIG. 24. FIG. 27 is an exploded perspective view illustrating the structure of the knot forming device 110 shown in FIG. 23. Note that the rotary operating member 16 shown in FIG. 27 has been omitted from the drawings in FIGS. 23 through 26.

The knot forming device 110 according to the second embodiment has a structure identical to the knot forming device 10 of the first embodiment, except a first movable member 148a, a fifth movable member 150a, a second movable member 148b, and a sixth movable member 150b are provided in place of the first movable member 48a, third movable member 50a, second movable member 48b, and fourth movable member 50b in the first embodiment. As in the first embodiment, the first movable member 148a and fifth movable member 150a of the second embodiment are disposed on the rear surface of the first arm 114a so as to be capably of moving along the longitudinal direction of the first arm 114a, and the second movable member 148b and sixth movable member 150b are disposed on the rear surface of the second arm 114b so as to be capable of moving along the longitudinal direction of the second arm 114b. Either the first movable member 148a and fifth movable member 150a or the second movable member 148b and sixth movable member 150b function as first and second guide members that guide the thread-like member L when tightening a know so that the thread-like member L on both sides of the knot is opened close to 180 degrees.

Since the first arm 114a and the first movable member 148a and fifth movable member 150a disposed on the rear surface of the first arm 114a so as to be longitudinally movable thereon have structures similar to the second arm 114b and the second movable member 148b and sixth movable member 150b disposed on the rear surface of the second arm 114b so as to be longitudinally movable thereon, only the first arm 114a and the first movable member 148a and fifth movable member 150a disposed on the rear surface of the first are 114a will be described below using reference numerals with the letter "a" thereto, while a description of the second arm 114b having the same reference numerals to which the letter "b" is appended will be omitted.

Figure 28:
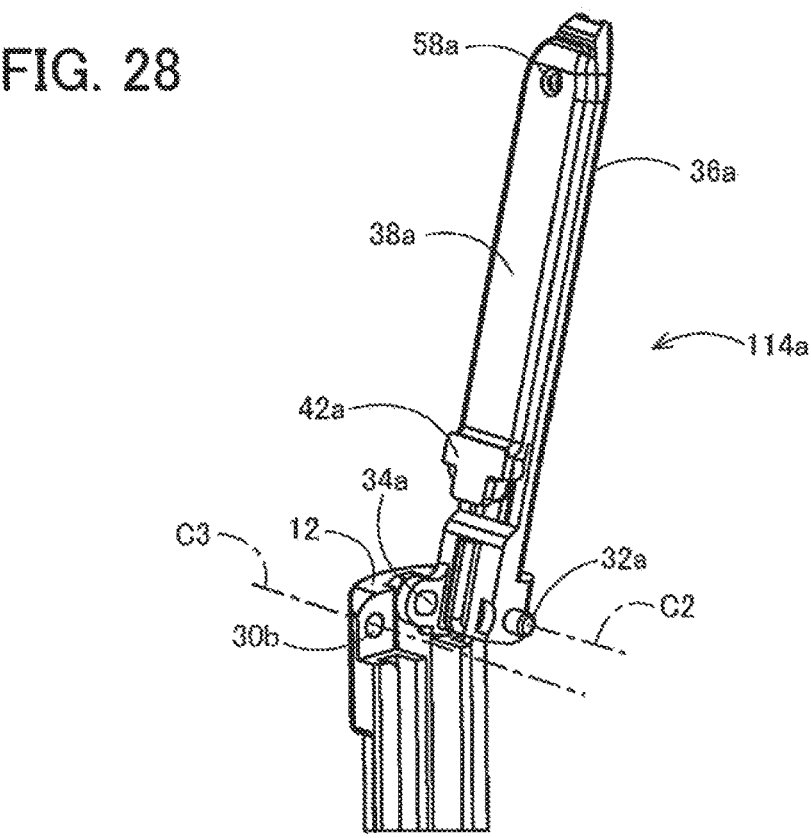
FIG. 28 is a perspective view showing the first arm of the knot forming device at an open position in the second embodiment.
Figure 29:
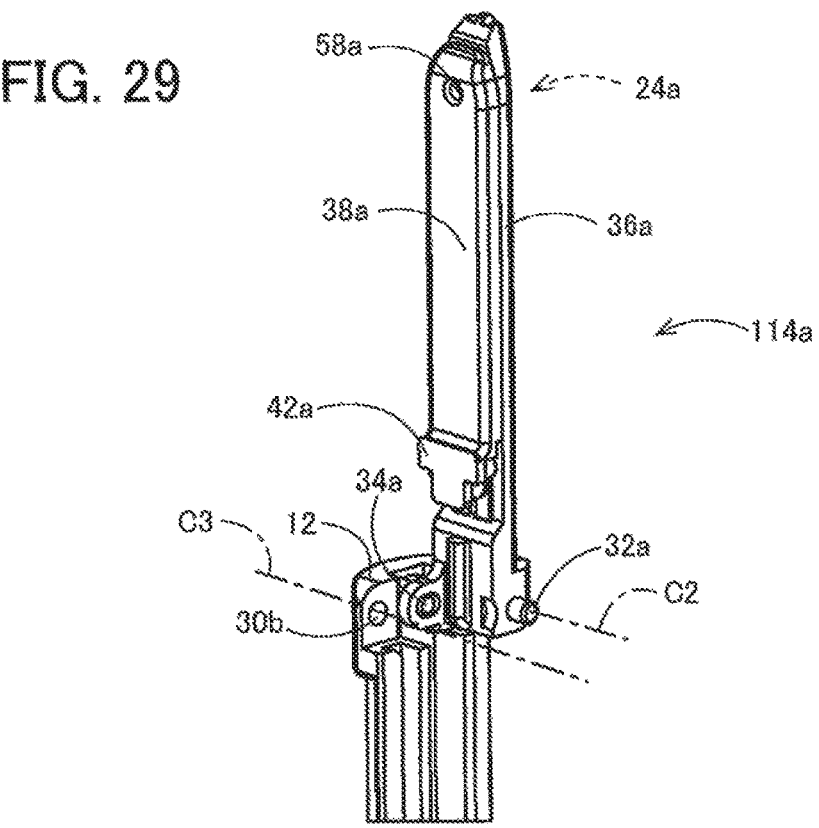
FIG. 29 is a perspective view showing the first arm of the knot forming device at a closed position in the second embodiment.
Figure 30:
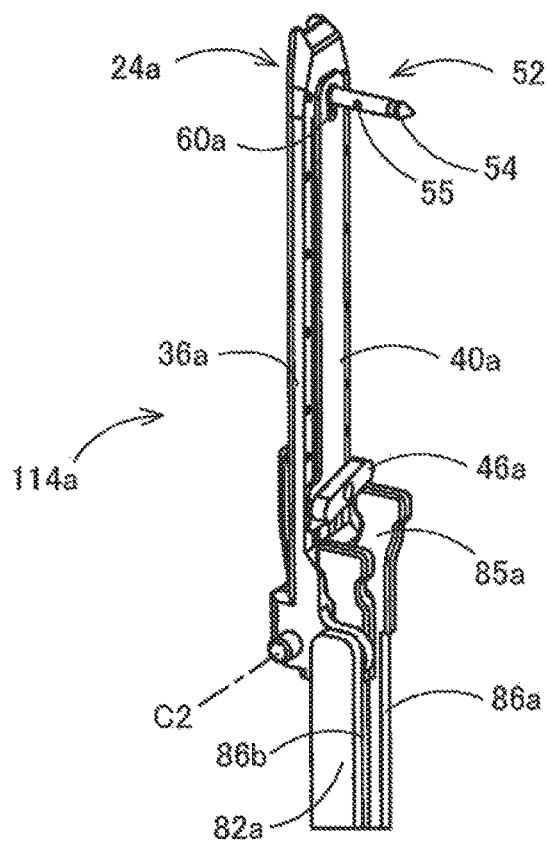
FIG. 30 is a perspective view showing the first arm of the knot forming device at the closed, position and a needle in a released state in the second embodiment, from which a guide cover is omitted.
Figure 31:
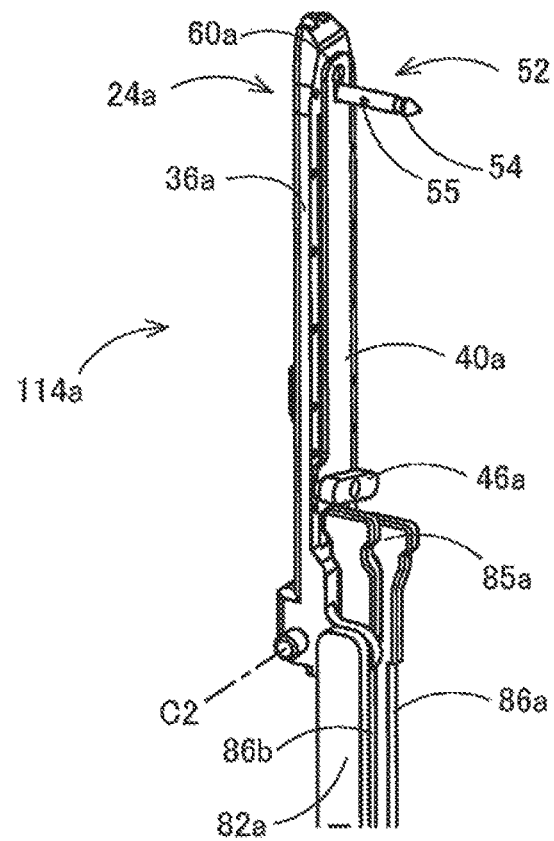
FIG. 31 is a perspective view showing the first am of the knot forming device at the closed position and the needle in a locked state in the second embodiment, from which the guide cover is omitted.
Figure 32:
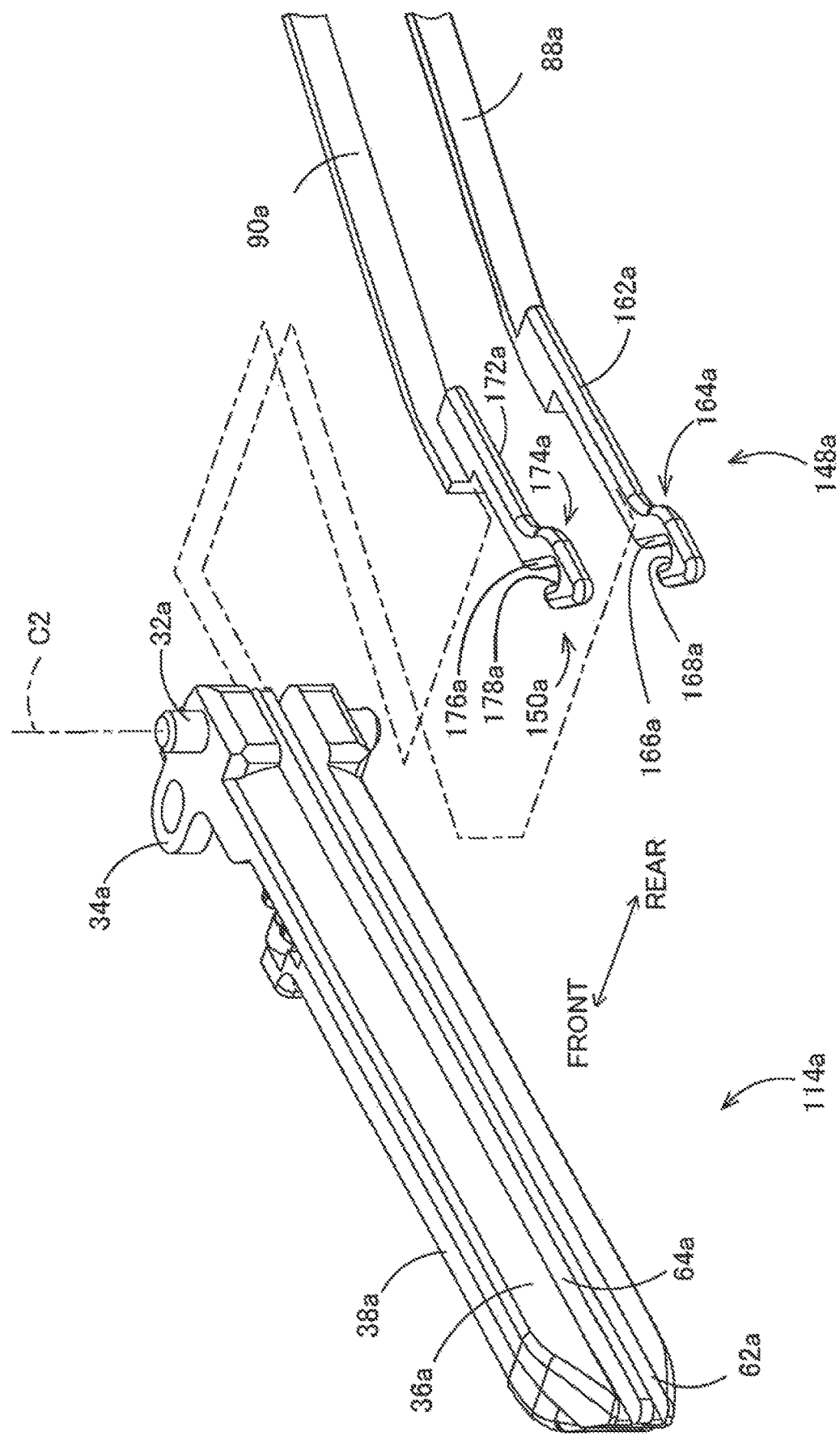
FIG. 32 is an enlarged perspective view illustrating a structure of the first arm of the knot forming device according to the second embodiment.
Figure 33:
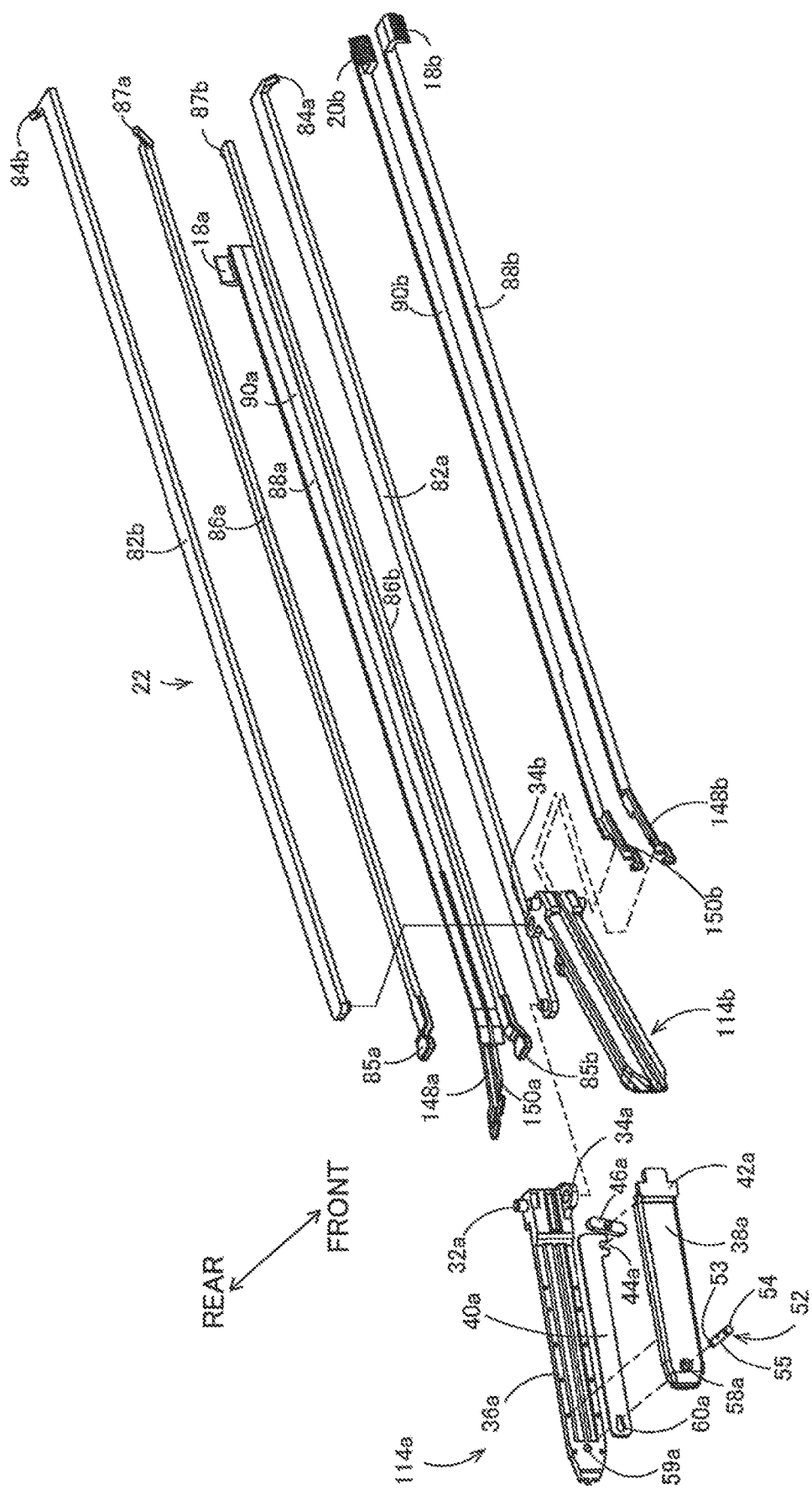
FIG. 33 is an exploded perspective view illustrating a structure of an operating force transmission mechanism of the knot forming device according to the second embodiment.

FIG. 28 shows the first arm 114a of the knot forming device 110 in its open state, and FIG. 29 shows the first arm 114a in its closed state. FIG. 30 is a perspective view showing the needle 52 in the released state in the first arm 114a while the first arm 114a is in the closed state, and FIG. 31 is a perspective view showing the needle 52 in the locked state in the first arm 114a. In FIGS. 30 and 31, the guide cover 38a has been omitted. FIG. 32 is an enlarged perspective view showing the rear surface of the first arm 114a and illustrating the structure of the first movable member 148a and fifth movable member 150a that are moved along the rear surface of the first arm 114a. In the present embodiment, both of the first movable member 148a and fifth movable member 150a correspond to the second moving portion in the claims, while both of the second movable member 148b and sixth movable member 150 correspond to the first moving portion in the claims.

As shown in FIG. 32, the first guide groove 62a and second guide groove 64a for guiding the first movable member 148a and fifth movable member 150a, respectively, are formed in the rear surface of the arm body 36a constituting the first arm 114a and are parallel to the longitudinal direction of the first arm 114a. The first movable member 148a includes a neck part 162a coupled to the distal end of the first flexible connecting plate 88a, and a hook part 164a formed by bending the distal end portion of the neck part 162a toward the first arm 114a in a hook-like shape. A sloped guiding surface 166a is formed on the hook part 164a, and a thread retaining notch 168a is formed in the hook part 164a. The sloped guiding surface 166a slopes away from the first arm 114a while advancing toward the distal end of the first arm 114a. The sloped guiding surface 166a receives the thread-like member L wrapped around the first arm 114a from the proximal side and guides the thread-like member L toward the second arm 114b side. The thread retaining notch 168a has a slope similar to the sloped guiding surface 166a and functions to retain the thread-like member L. Similarly, the fifth movable member 150a includes a neck part 172a coupled to a distal end of the first flexible connecting plate 88a, and a hook part 174a formed by bending the distal end portion of the neck part 172a toward the that arm 114a in a hook-like shape. A sloped guiding surface 176a is formed on the hook part 174a, and a thread retaining notch 178a is formed in the hook part 174a. The sloped guiding surface 176a slopes away from the first arm 114a while advancing toward the distal end side of the first arm 114a. The sloped guiding surface 176a receives the thread-like member L wrapped around the first arm 114a from the proximal side and guides the thread-like member L toward the second arm 114b side. The thread retaining notch 178a has a similar slope to the sloped guiding surface 176a and functions to retain the thread-like member L. As described above, the first movable member 148a is guided by the first guide groove 62a. At this time, the distal end of the hook part 164a provided on the first movable member 148a is fitted in the first guide groove 62a. The thread-like member L is retained inside the thread retaining notch 168a as long as the first movable member 148a does not move beyond the distal end of the first arm 114a. Similarly, the fifth movable member 150a is guided by the second guide groove 64a, at which the distal end of the hook part 174a provided on the fifth movable member 150a is fitted in the second guide groove 64a. The thread-like member L is retained in the thread retaining notch 178a as long as the fifth movable member 150a does not move beyond the distal end of the first arm 114a. Further, the neck part 162a of the first movable member 148a is formed longer than the neck part 172a of the fifth movable member 150a. Thus, when retained on the first arm 114a, thread-like member L within the thread retaining notch 168a is always positioned closer to the distal end of the first arm 114a than thread-like member L within the thread retaining notch 178a.

Figure 34:
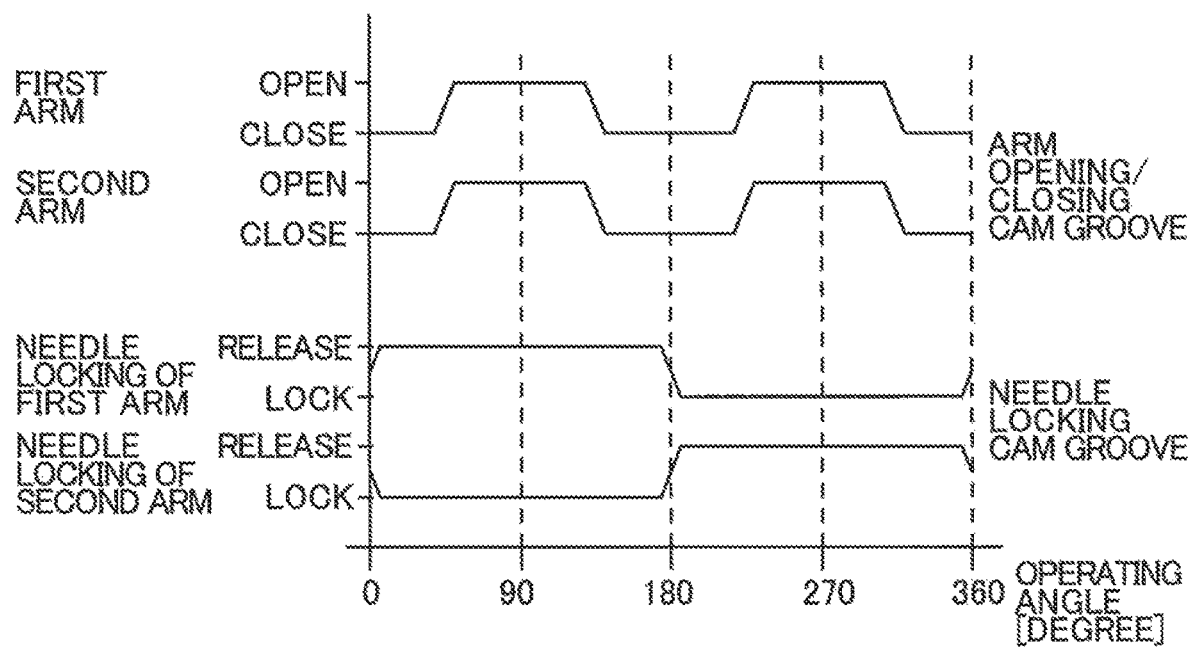
FIG. 34 is a chart illustrating a relationship between an operating angle of a rotary operating member of the knot forming device, and an opening and closing operation for the first arm and the second arm and a locking and leasing operation for the needle in the second embodiment.

FIG. 34 is a chart illustrating the relationships between the operating angle of the rotary operating member 16 disposed on the knot forming device 110, and the opening and closing operations for the first arm 114a and second arm 114b and the locking and releasing operations for the needle 52 actuated by the rotating operation of the rotary operating member 16. As in the chart of FIG. 12, the horizontal axis in FIG. 34 represents the angle through which the rotary operating member 16 is rotated in a right-handed turn from the orientation in FIG. 1. FIG. 28 shows the position of the first arm 114a after the rotary operating member 16 has been rotated about 135 degrees from the point of origin on the horizontal axis in FIG. 34, and FIG. 29 shows the position of the first arm 114a after the rotary operating member 16 has been rotated about 45 degrees. This operation of rotating the rotary operating member 16 may be a manual operation or a remote operation using the drive of a motor to rotate the rotary operating member 16.

As shown in FIG. 34, the operation for rotating the rotary operating member 16 is performed with the knot forming device 110 having the above structure in order to implement the operations of opening and closing the first arm 114a and second arm 114b and transferring the needle 52 between the first arm 114a and second arm 114b. Other operations performed in relation to these operations are a wrapping operation for wrapping the thread-like member L around the first arm 114a and second arm 114b through the operation of the outer sleeve 26, and a thread removing operation performed by manually operating either the linear operating members 18a and 20a or the linear operating members 18b and 20b. These operations semiautomatically form a knot in the thread-like member L. Next, the operations of the knot forming device 110 according to the second embodiment will be described in greater detail with reference to FIGS. 35, 36, and 37.

Figure 35:
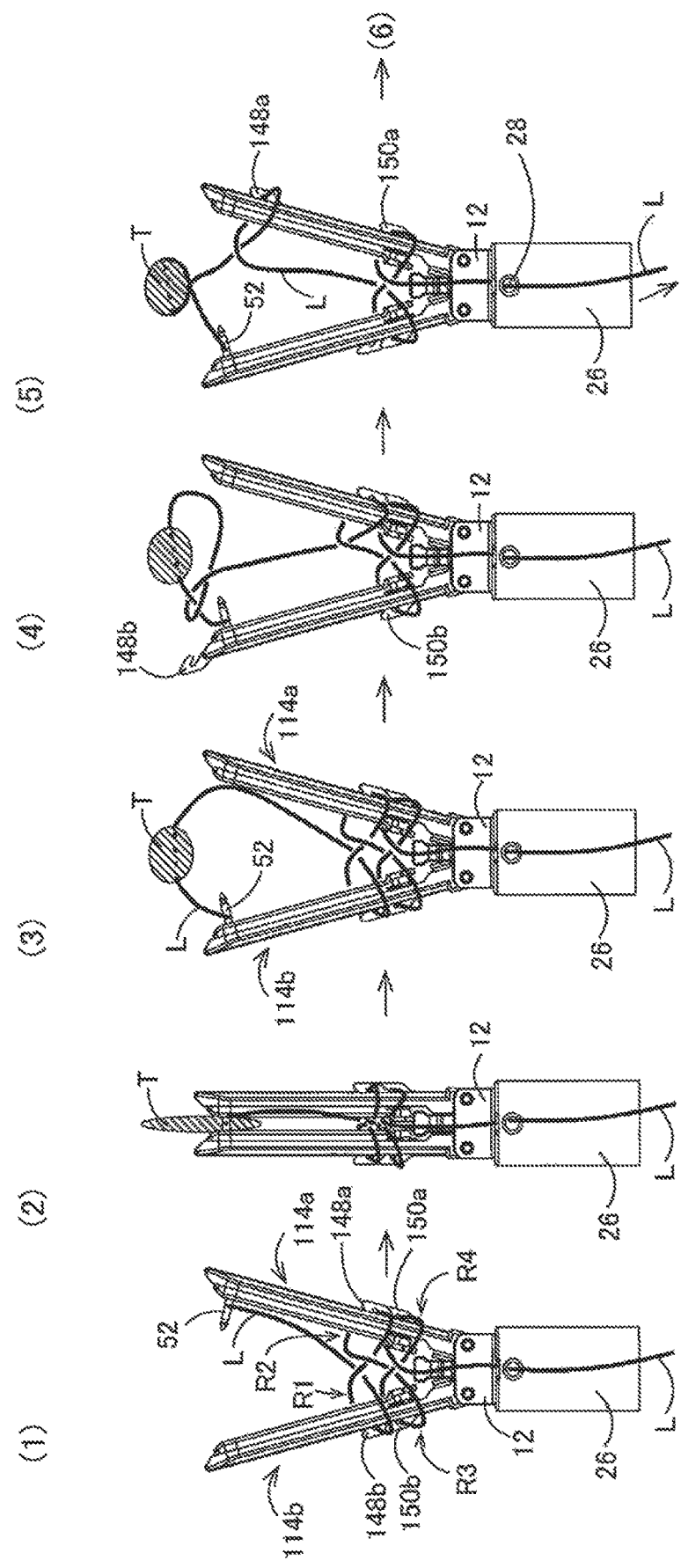
FIG. 35 is an explanatory diagram illustrating a part of steps in a knot forming operation performed by the knot forming device according to the second embodiment.

Steps (1) through (5) of FIG. 35 show an operation for forming a knot in a first throw. Step (1) in FIG. 35 shows the initial state of the knot forming device 110 in a knot finning operation. The knot forming device 110 according to the second embodiment is shipped from the factory or provided to the user in an initial state wherein the thread-like member L is pre-wrapped about the first arm 114a and second arm 114b, as shown in (1) of FIG. 35, for example. Alternatively, the distal end portion of the knot forming device 110 may be detachable from the elongate base member 12 and may be shipped from the factory or provided to the user in the state shown in (1) of FIG. 35. In this initial state, the first movable member 148a and fifth movable member 150a are positioned on the proximal end of the first arm 114a and the second movable member 148b and sixth movable member 150b are positioned on the proximal end of the second arm 114b, while the first arm 114a and second arm 114b are in an open state for the interval in which the operating angle of the rotary operating member 16 moves from 45 degrees to near 135 degrees, far example. Further, the needle 52 is fixed in the first needle locking mechanism 24a of the first arm 114a, and the thread-like member L fixed at me end to the needle 52 is passed through the thread guiding hole 28 of the outer sleeve 26. Also, two loops are preformed in the thread-like member L about each of the first arm 114a and second arm 114b in this initial state. Specifically, from the needle 52 locked in the first arm 114a to the thread guiding hole 28 thrilled in the outer sleeve 26, the thread-like member L forms a first loop R1 wrapped around the second arm 114b and retained by the second movable member 148b, followed sequentially by a second loop R2 wrapped around the first arm 114a and retained by the first movable member 148a, a third loop R3 wrapped around the second arm 114b and retained by the sixth movable member 150b, and a fourth loop R4 wrapped around the first arm 114a and retained by the fifth movable member 150a.

Next, by rotating the rotary operating member 16 until its rotated angle reaches approximately 135 degrees, for example the first arm 114a and second arm 114b close around the tissue T, as shown in (2) of FIG. 35. At this time, the second end of the needle 52 passes through the tissue T and is received in and locked by the second needle locking mechanism 24b of the second arm 114b, while the first end of the needle 52 that was locked in the first needle locking mechanism 24a of the first arm 114a is released (unlocked). Next, the first arm 114a and second arm 114b are opened by continuing to rotate the rotary operating member 16 until its rotated angle passes near 225 degrees, for example. Step (3) of FIG. 35 shows this state. Subsequently, the linear operating member 18b is operated to move the second movable member 148b of the second arm 114b from its proximal position to its distal position on the second arm 114b, pushing the first loop R1 off the distal end of the second arm 114b, as illustrated in (4) of FIG. 35. Next, the second movable member 148b of the second arm 114b is returned from its distal position to its proximal position on the second arm 114b, and the first movable member 148a is moved from its proximal position on the first arm 114a to a position toward the distal and without allowing the thread retaining notch 168a to be exposed beyond the distal end of the first arm 114a, as indicated in (5) of FIG. 35. In this state, the thread-like member L is pulled at the fourth position, which is the portion of the thread-like member L passing through the thread guiding hole 28 of the outer sleeve 26 to the rotary operating member 16 side, thereby tightening the knot. The knot formed in this example is the overhand knot M1 shown in FIG. 18.

Figure 36:
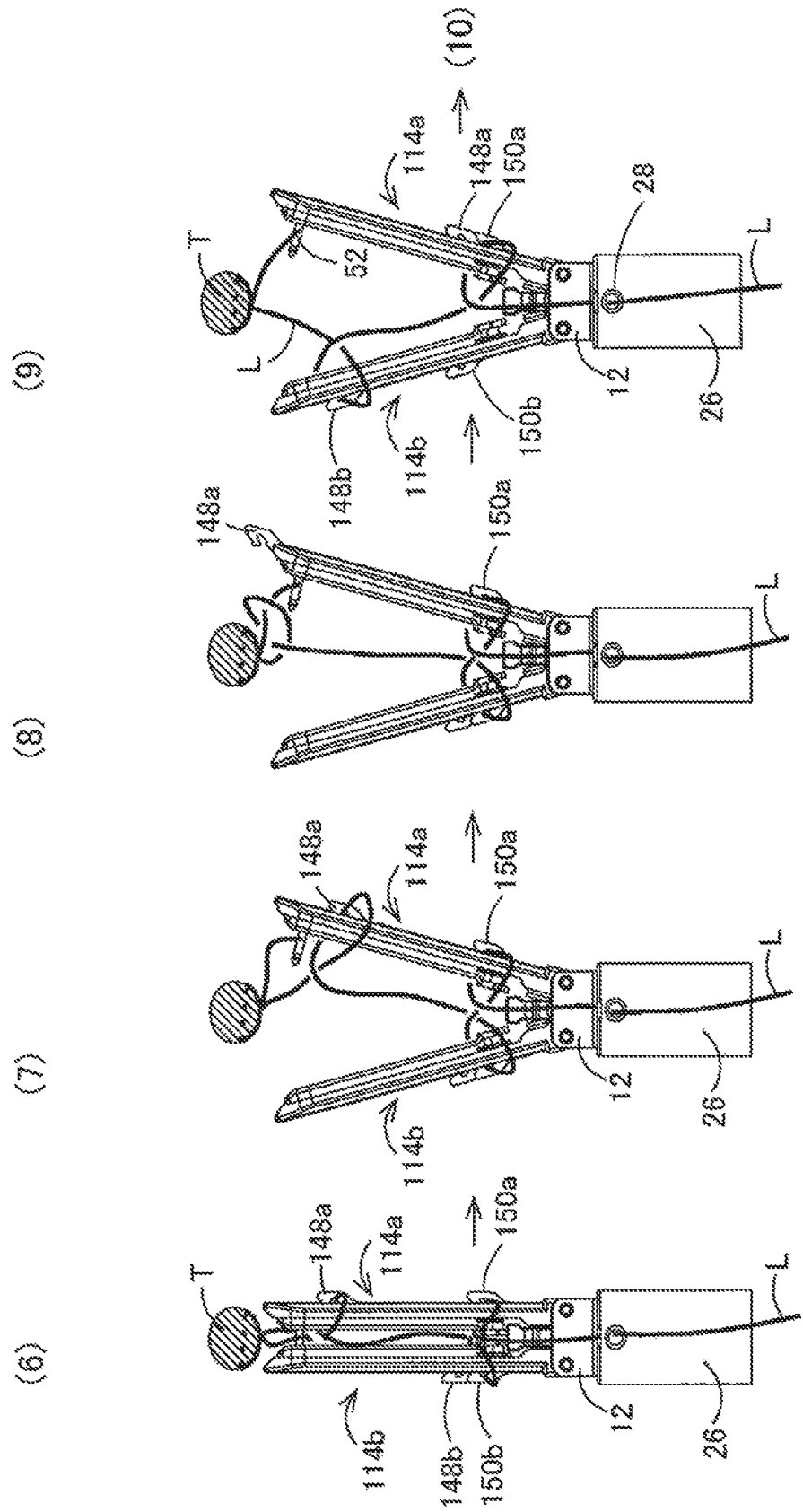
FIG. 36 is an explanatory diagram illustrating a part of steps in the knot forming operation performed subsequent to the steps illustrated in FIG. 35 by the knot forming device according to the second embodiment.

Steps (6) through (9) of FIG. 36 show the operation for forming a knot in the second throw. After completing knot formation for the first throw, the rotary operating member 16 is rotated until its rotated angle reaches approximately 315 degrees, causing the first arm 114a and second an 114b close without the tissue T interposed therebetween, as illustrated in (6) of FIG. 36, and the needle 52 locked on the second arm 114b is transferred by being unlocked from the second arm 114b side and looked in the first arm 114a side. Next, the rotary operating member 16 is rotated until its angle reaches approximately 405 degrees, for example, opening the first arm 114a and second arm 114b illustrated in (7) of FIG. 36. Subsequently, the linear operating member 18a is operated to move the first movable member 148a of the first arm 114a to its distal position on the first arm 114a, pushing the second loop R2 off the distal end of the first arm 114a, as illustrated in (8) of FIG. 36. Through this operation, the first position of the thread-like member L passes through the loop for forming a knot in the second throw from the sixth position side to the fifth position side, where the fifth position (third intersecting position) is the intersecting point of the loop between the first position and fourth position of the thread-like member L and the sixth position (fourth intersecting position) is the intersecting point positioned farther than the fifth position from the first position. This loop for forming the second throw of the knot is wrapped around a second path extending from the second retaining position of the second retaining member provided on the second arm 114b to the fourth position of the thread-like member L along the second arm 114b and first arm 114a (the device body). Further, the loop for forming the second throw of the knot intersects at a fifth position between the first position and fourth position of the thread-like member L and a sixth position that is farther than the fifth position from the first position such that the sixth position is closer to the second retaining position of the second retaining member disposed on the second an 114b than the fifth position along the second path. Next, the second movable member 148b is moved from its proximal position on the second arm 114b toward the distal end of the second arm 114b to a point that does not expose the thread retaining notch 168b above the distal end of the second arm 114b, thereby preventing the eighth position of the thread-like member L from coining off the second arm 114b, as shown in (9) of FIG. 36. In this state, the thread-like member L is pulled at the fourth position, which is the portion of the thread-like member L that is passed through the thread guiding hole 28 of the outer sleeve 26 to the rotary operating member 16 side, thereby tightening the knot. The knot formed through this operation is the square knot M4 shown in FIG. 21.

Figure 37:
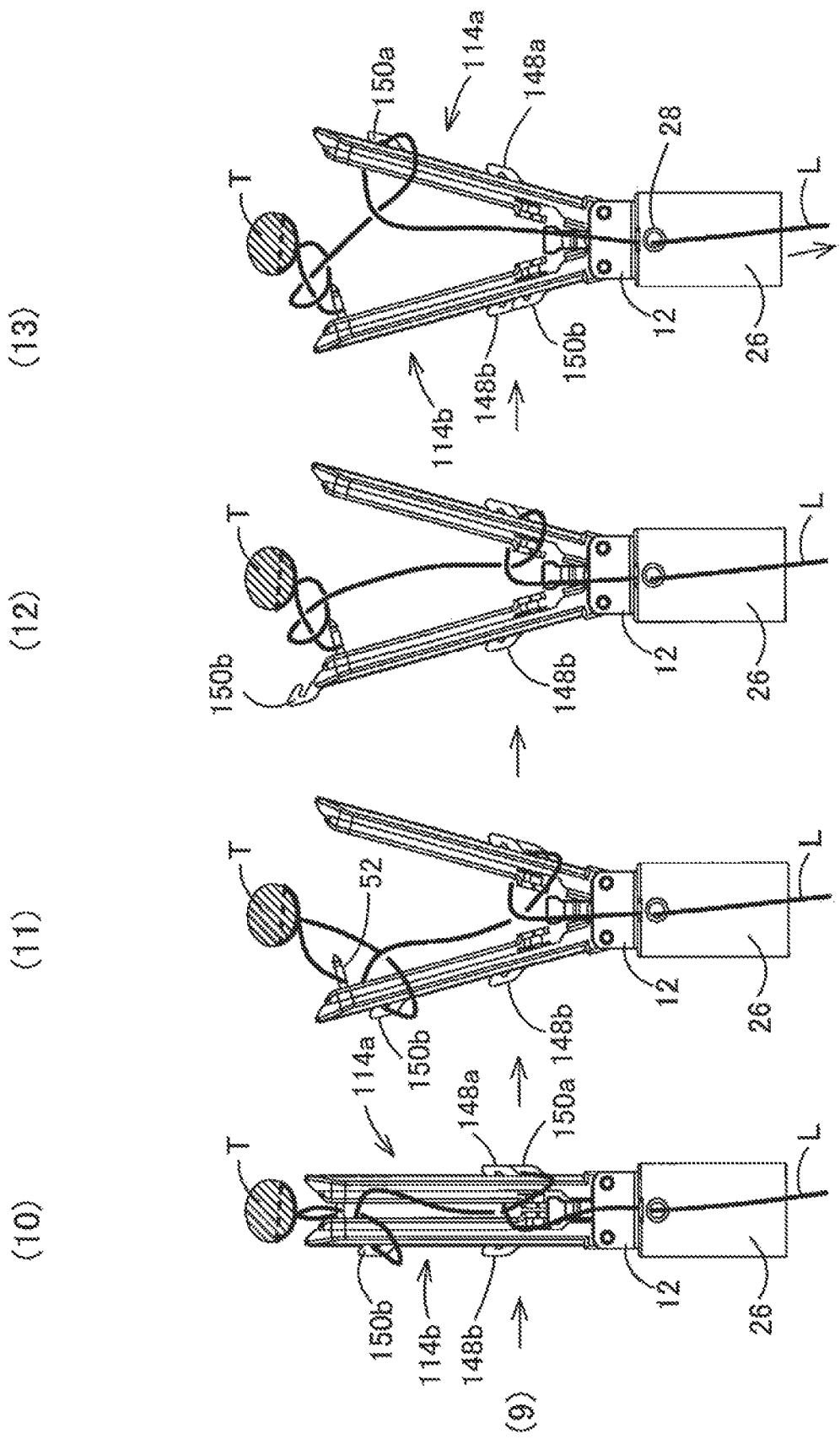
FIG. 37 is an explanatory diagram illustrating apart of steps in the knot forming operations performed subsequent to the steps illustrated in FIG. 36 by the knot forming device according to the second embodiment.

Steps (10) through (13) of FIG. 37 show an operation for forming a knot in a third throw. As shown in (10) of FIG. 37, the rotary operating member 16 is rotated until its rotated angle reaches approximately 45 degrees, for example, closing the first arm 114a and second arm 114b without the tissue T interposed therebetween. At this time, the second end of the needle 52 is received in and locked by the second needle locking mechanism 24b on the second arm 114b, while the first end locked in the first needle locking mechanism 24a is released (unlocked). Next, the rotary operating member 16 is rotated until its rotated angle reaches approximately 585 degrees, for example, opening the first arm 114a and second arm 114b, as illustrated in (11) of FIG. 37. Next, the linear operating member 20b is operated to move the sixth movable member 150b of the second arm 114b to its distal position on the second arm 114b, removing the third loop R3 from the distal end of the second arm 114b, as shown in (12) of FIG. 37. Subsequently, the fifth movable member 150a is moved from its proximal position on the first arm 114a toward the distal side up to a position at which the thread retaining notch 168a is not exposed beyond the distal end of the first arm 114a, as shown in (13) of FIG. 37. In this state, the thread-like member L is pulled by the portion passed through the thread guiding hole 28 of the outer sleeve 26 to the rotary operating member 16 side, forming a knot for the third throw. The knot for the fourth throw is formed similarly to that for the third throw by moving the fourth loop R4 using the same operations for the third throw, but exchanging left and right in the description. While the knot forming device 110 according to the second embodiment described above retains loops for four throws that are prepared in advance, another device may be configured to form knots in any desired number of throws according to the same principles by simply increasing the number of prepared loops and the number of movable members.

Figure 38:
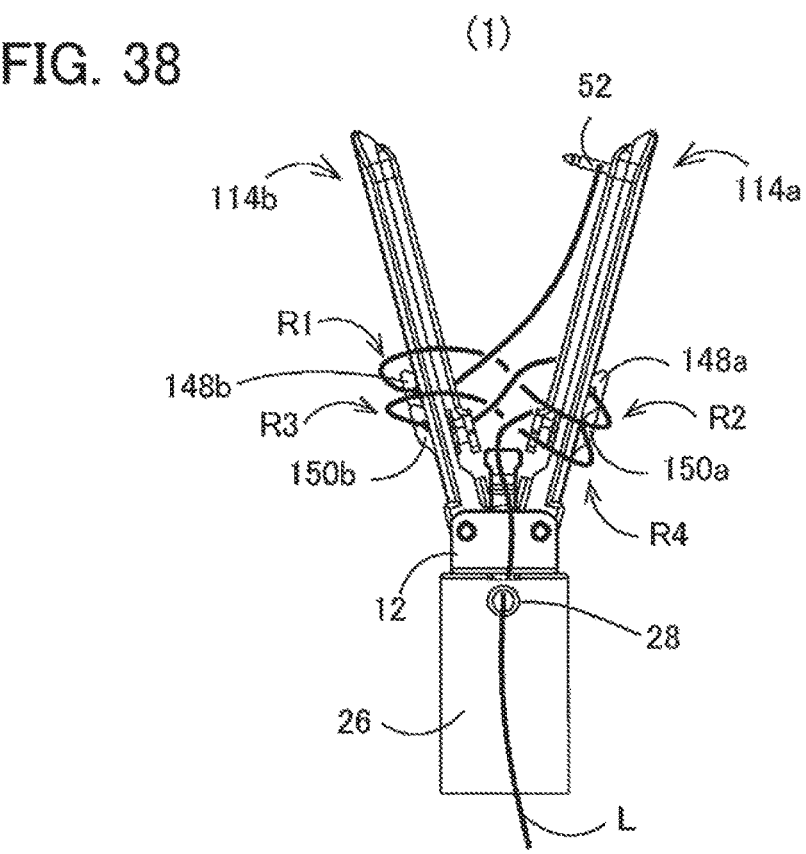
FIG. 38 is an explanatory diagram illustrating another example of an initial state of the knot forming device shown in (1) of FIG. 35.

As shown in (1) of FIG. 38, the relative relationship between a first wrapping direction in which the first loop R1 is wrapped around the second arm 114b and a second mapping direction in winch the second loop R2 is wrapped around the first arm 114a may be opposite the relative relationship between the first wrapping direction and the second wrapping direction shown in (1) of FIG. 35 for example. In this case, the double-throw knot of in (9) of FIG. 36 would be the granny knot M3 shown in FIG. 20. Further, if the first loop R1 were wrapped twice around the second arm 114b in (1) of FIG. 35, the single-throw knot obtained in (5) of FIG. 35 would be the double overhand knot M2 shown in FIG. 19.

In addition to obtaining the same effects described for the knot forming device 10 in the first embodiment, the knot forming device 110 according to the second embodiment is provided with the second arm 114b (the first loop retaining member) that retains preformed loops. Providing preformed loops on the second arm 114b in this way eliminates the time and effort required for forming such loops on the scene and the need for a mechanism to form the loops thereby simplifying the knot forming device 110.

According to the knot forming device 110 of the present embodiment, the first arm 114a (the second loop retaining member) also retains performed loops. Providing preformed loops on the first arm 114a in this way eliminates the time and effort required for forming such loops on the scene and the need or a mechanism to form the loops, thereby simplifying the knot forming device 110.

Figure 39:
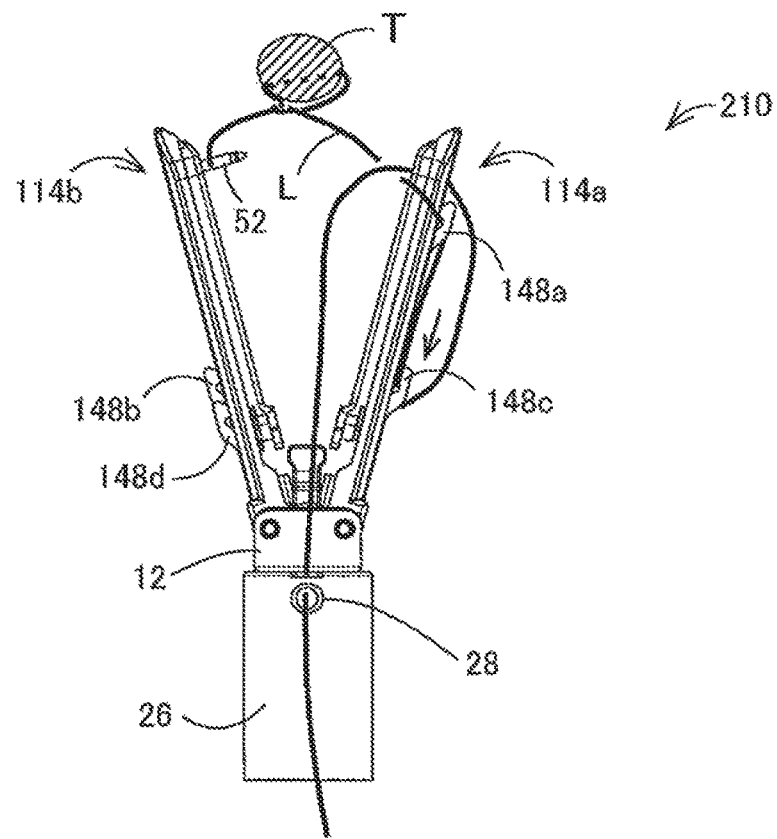
FIG. 39 is an explanatory diagram illustrating another example of a tightening operation shown in (5) of FIG. 35 or (13) of FIG. 37 performed by a knot forming device according to a variation of the second embodiment.

FIG. 39 shows a knot forming device 210 according to a variation of the second embodiment. While the know forming device 110 according to the second embodiment is provided with one guide member for each loop, the knot forming device 210 according to the variation is provided with two guide members for each loop. In other words, other than the thread-like member L, the mechanical structure of the knot forming device 210 is essentially identical to the knot forming device 110 of the second embodiment. However, the thread-like member L is pre-wrapped such that the second loop R2 is retained by both the first movable member 148a and a seventh movable member 148c. FIG. 39 shows the state in which the seventh movable member 148c has been moved back toward the proximal side of the first arm 114a after both the first movable member 148a and seventh movable member 148c were moved from the proximal position on the first arm 114a toward the distal side up until a point at which the thread retaining notch 168a is not exposed beyond the distal end of the first arm 114a. This operation causes the seventh movable member 148c to pull the loop at a midpoint thereof, tightening the knot. The operation is performed in place of the knot tightening operation shown in (5) of FIG. 35. For the third loop R3, if a thread-like member is pre-wrapped to form the loop R3 held by both the second movable member 148b and an eighth movable member 148d, an operation for moving the eighth movable member 148d toward the proximal side of the second arm 114b may be performed in place of the knot tightening operation shown in (13) of FIG. 37 for tightening the knot. All other configurations and operations excluding this knot tightening operation are identical to those performed by the knot forming device 110 of the second embodiment and, hence, a description of these operations has been omitted. With the structure of this variation, it is possible to directly pull on the thread-like member L at a position near the knot, thereby tightening the knot more reliably with less force due to the elimination of friction generated by the thread guiding hole 28 and the other loops than when pulling the thread-like member at the fourth position, as in the knot forming devices 10 and 110 in the embodiments described above.

While specific embodiments of the present disclosure have been described with reference to the drawings, the present disclosure may be implemented in other forms.

For example, the thread-like member L in the embodiments described above may be any of various tying medium that can be tied, and preferably natural sutures formed by braiding natural plant-based or animal-based fibers, polymer sutures formed of monofilament or braided strands of synthetic fibers, metallic sutures formed of monofilament or braided metallic strands, or composite sutures formed of natural and synthetic fibers.

Further, the needle 52 may be formed or metal, synthetic resin, natural material, and the like, provided that the needle-like member is formed of a material with sufficient hardness. Further, white the needle 52 in the embodiments is held by inserting locking members into notches formed in the needle 52, the needle 52 may be configured without notches and may be held direction instead. In this case, the needle 52 need not be provided on the end of the thread-like member L and the thread-like member L may be gripped directly instead. The strength of the thread like member L may be partially modified by applying a paste-like material to the ends of the thread-like member L to permeate and solidify therein, for example.

Although other examples of the disclosure will not be illustrated herein, the disclosure can be implemented in variously modified or refined forms based on the knowledge of those skilled in the art.

What is claimed is:

1. A knot forming device configured to form a knot in a tying medium, the knot forming device comprising:
    a base part extending in a first direction;
    a first arm disposed on the base part and having a first retaining member configured to detachably retain a first position of the tying medium at a first retaining position;
    a second arm disposed on the base part and having a second retaining member configured to detachably retain the first position of the tying medium at a second retaining position instead of the first retaining member;

a switching mechanism configured to switch a retained state of the first position of the tying medium between a first state where the first position is retained by the first retaining member at the first retaining position and a second state where the first position is retained by the second retaining member at the second retaining position;

the second arm functioning as a first loop retaining member configured to retain a first loop around the second arm in a first path of the tying medium, the first path extending from the first retaining position through a second position and a third position to a fourth position of the tying medium, the second position of the tying medium intersecting the third position of the tying medium as a result of the first loop such that the third position is downstream of the second position in a direction of the first path, and is closer to the first retaining position than the second position is to the first retaining position in the first path;

a first moving portion configured to move the first loop relative to the second arm in synchronism with the switching operation of the switching mechanism from the first state to the second state to thus change a relative positional relationship between the first loop and the first position of the tying medium on the first path;

the first arm functioning as a second loop retaining member configured to retain a second loop around the first arm in a second path of the tying medium, the second path extending from the second retaining position through a fifth position and a sixth position to the fourth position of the tying medium, the fifth position of the tying medium intersecting the sixth position of the tying medium as a result of the second loop such that the sixth position is downstream of the fifth position in a direction of the second path, and is closer to the second retaining position than the fifth position to the second retaining position in the second path;

a second moving portion configured to move the second loop relative to the first arm in synchronism with the switching operation of the switching mechanism from the second state to the first state to thus change a relative positional relationship between the second loop and the first position of the tying medium on the second path; and an operating part configured to operate the switching mechanism, the moving portion, and the second moving portion.

2. The knot forming device according to claim 1, wherein the first loop around the second arm in a third path of the tying medium is wrapped in a direction opposite the second loop around the first arm in the third path of the tying medium, the third path extending from the base part through the second retaining member and the first retaining member to the base part.

3. The knot forming device according to claim 1, wherein the first loop around the second arm in a third path of the tying medium is wrapped in a direction same as the second loop around the first arm in the third path of the tying medium, the third path extending from the base part through the second retaining member and the first retaining member to the base part.

4. The knot forming device according to claim 1, wherein the first loop around the second arm is wrapped twice in the first path, and the second loop around the first arm is wrapped once in the second path.

5. The knot forming device according to claim 1, further comprising:

a loop forming member configured to form the first loop around the first loop retaining member in the first path of the tying medium such that the third position is closer to the first retaining position than the second position is to the first retaining position in the first path.

6. The knot forming device according to claim 5, wherein the first loop retaining member retains the first loop by wrapping the tying medium around a portion between the base part and the second retaining member of the second arm in the first path, and wherein the loop forming member comprises:
a rotating member configured to rotate the first arm and the second arm relative to the fourth position of the tying medium so as to wrap the tying medium around an axis extending in the first direction; and
a third moving portion configured to move the tying medium wrapped around the axis relative to the first retaining position along the first path such that the first loop is wrapped around the first loop retaining member.

7. The knot forming device according to claim 1, further comprising:

a loop forming member configured to form the second loop around the second loop retaining member in the second path of the tying medium such that the sixth position is closer to the second retaining position than the fifth position is to the second retaining position in the second path.

8. The knot forming device according to claim 7, wherein the second loop retaining member retains the second loop by wrapping the tying medium around a portion between the base part and the first retaining member of the first arm in the second path, and wherein the loop forming member comprises:
a rotating member configured to rotate the first arm and the second arm relative to the fourth position of the tying medium so as to wrap the tying medium around an axis extending in the first direction; and
a third moving portion configured to move the tying medium wrapped around the axis relative to the second retaining member along the second path such that the second loop is wrapped around the second loop retaining member.

9. The knot forming device according to claim 1, wherein the first moving portion moves the tying medium in a direction separating from the base part in the first path.

10. The knot forming device according to claim 1, wherein the second moving portion moves the tying medium in a direction separating from the base part in the second path.

11. The knot forming device according to claim 1, further comprising a first guide member capable of moving the tying medium in a direction separating from the base part in the first path, the first guide member being configured to support a seventh position of the tying medium contacting the first arm while restraining movement of the seventh position at a position separated from the base part by at least a first distance.

12. The knot forming device according to claim 11, wherein the first guide member is capable of moving the tying medium in a direction approaching the base part in the first path, the first guide member being configured to support the seventh position of the tying medium while restraining movement of the seventh position at a position separated from the base part by at most a second distance greater than the first distance.

13. The knot forming device according to claim 11, wherein the first guide member has a guide surface provided on a side farther from the base part and configured to support the seventh position of the tying medium from a base part side.

14. The knot forming device according to claim 13, wherein the second moving portion functions as the first guide member.

15. The knot forming device according to claim 11, further comprising a second guide member capable of moving the tying medium in a direction separating from the base part in the second path, the second guide member being configured to support an eighth position of the tying medium contacting the second arm while restraining movement of the eighth position at a position separated from the base part by at least a third distance.

16. The knot forming device according to claim 15, wherein the second guide member is capable of moving the tying medium in a direction approaching the base part in the second path, the second guide member being configured to support the eighth position of the tying medium while restraining movement of the eighth position at a position separated from the base part by at most a fourth distance greater than the third distance.

17. The knot forming device according to claim 15, wherein the second guide member has a guide surface provided on a side farther from the base part and configured to support the eighth position of the tying medium from a base part side.

18. The knot forming device according to claim 17, wherein the first moving portion functions as the second guide member.

19. A knot forming device configured to form a knot in a tying medium, the knot forming device comprising:
a base part extending in a first direction;
a first arm disposed on the base part and having a first retaining member configured to detachably retain a first position of the tying medium at a first retaining position;
a second arm disposed on the base part and having a second retaining member configured to detachably retain the first position of the tying medium at a second retaining position instead of the first retaining member;
a switching mechanism configured to switch a retained state of the first position of the tying medium between a first state where the first position is retained by the first retaining member at the first retaining position and a second state where the first position is retained by the second retaining member at the second retaining position;
the second arm functioning as a first loop retaining member configured to retain a first loop around the second arm in a first path of the tying medium, the first path extending from the first retaining position through a second position and a third position to a fourth position of the tying medium, the second position of the tying medium intersecting the third position of the tying medium as a result of the first loop such that the third position is downstream of the second position in a direction of the first path, and is closer to the first retaining position than the second position is to the first retaining position in the first path; and
a first moving portion configured to move the first loop relative to the second arm in synchronism with the switching operation of the switching mechanism from the first state to the second state to thus change a relative positional relationship between the first loop and the first position of the tying medium on the first path;
an operating part configured to operate the switching mechanism and the first moving portion,
wherein the second arm is movable relative to the first arm in a second direction orthogonal to the first direction, and
wherein the operating part is further configured to bring the first arm and the second arm into contact with each other and separate the first arm and the second arm from each other.

20. The knot forming device according to claim 19, wherein the first moving portion moves the tying medium in a direction separating from the base part in the first path.

21. A knot forming device configured to form a knot in a tying medium, the knot forming device comprising:
a base part extending in a first direction;
a first arm disposed on the base part and having a first retaining member configured to detachably retain a first position of the tying medium at a first retaining position;
a second arm disposed on the base part and having a second retaining member configured to detachably retain the first position of the tying medium at a second retaining position instead of the first retaining member;
a switching mechanism configured to switch a retained state of the first position of the tying medium between a first state where the first position is retained by the first retaining member at the first retaining position and a second state where the first position is retained by the second retaining member at the second retaining position;
the second arm functioning as a first loop retaining member configured to retain a first loop around the second arm in a first path of the tying medium, the first path extending from the first retaining position through a second position and a third position to a fourth position of the tying medium, the second position of the tying medium intersecting the third position of the tying medium as a result of the first loop such that the third position is downstream of the second position in a direction of the first path, and is closer to the first retaining position than the second position is to the first retaining position in the first path;
a first moving portion configured to move the first loop relative to the second arm in synchronism with the switching operation of the switching mechanism from the first state to the second state to thus change a relative positional relationship between the first loop and the first position of the tying medium on the first path; and
an operating part configured to operate the switching mechanism and the first moving portion, wherein the operating portion is configured to perform:
a first moving operation for bringing the first arm and the second arm into contact with each other;
a switching operation for switching the retained state of the first position of the tying medium from the first state to the second state;
a second moving operation for separating the first arm and the second arm from each other to open the first arm and the second arm; and a loop moving operation for controlling the first moving portion to move the first loop along the first path in a direction toward the second retaining position.

22. The knot forming device according to claim 21, wherein the first moving portion moves the tying medium in a direction separating from the base part in the first path.

23. A knot forming device configured to form a knot in a tying medium, the knot forming device comprising:

a base part extending in a first direction;

a first arm disposed on the base part and having a first retaining member configured to detachably retain a first position of the tying medium at a first retaining position;

a second arm disposed on the base part and having a second retaining member configured to detachably retain the first position of the tying medium at a second retaining position instead of the first retaining member;

a switching mechanism configured to switch a retained state of the first position of the tying medium between a first state where the first position is retained by the first retaining member at the first retaining position and a second state where the first position is retained by the second retaining member at the second retaining position;

the second arm functioning as a first loop retaining member configured to retain a first loop around the second arm in a first path of the tying medium, the first path extending from the first retaining position through a second position and a third position to a fourth position of the tying medium, the second position of the tying medium intersecting the third position of the tying medium as a result of the first loop such that the third position is downstream of the second position in a direction of the first path, and is closer to the first retaining position than the second position is to the first retaining position in the first path;

a first moving portion configured to move the first loop relative to the second arm in synchronism with the switching operation of the switching mechanism from the first state to the second state to thus change a relative positional relationship between the first loop and the first position of the tying medium on the first path; and an operating part configured to operate the switching mechanism and the first moving portion, wherein the operating part is configured to form the knot by controlling the first moving portion to shift an orientation of the tying medium from a first orientation to a second orientation through a third orientation, the first position of the tying medium being retained by the first retaining member at the first retaining position and separated from the second retaining member in the first orientation, a loop nearest the first position being retained by the first loop retaining member in the first orientation, the first position being retained by the second retaining member at the second retaining position and separated from the first retaining member in the second orientation, the first position contacting both the first retaining member and the second retaining member in the third orientation.

24. The knot forming device according to claim 23, wherein the first moving portion moves the tying medium in a direction separating from the base part in the first path.

25. A knot forming device configured to form a knot in a tying medium, the knot forming device comprising:

a base part extending in a first direction;

a first arm disposed on the base part and having a first retaining member configured to detachably retain a first position of the tying medium at a first retaining position;

a second arm disposed on the base part and having a second retaining member configured to detachably retain the first position of the tying medium at a second retaining position instead of the first retaining member;

a switching mechanism configured to switch a retained state of the first position of the tying medium between a first state where the first position is retained by the first retaining member at the first retaining position and a second state where the first position is retained by the second retaining member at the second retaining position;

the second arm functioning as a first loop retaining member configured to retain a first loop around the second arm in a first path of the tying medium, the first path extending from the first retaining position through a second position and a third position to a fourth position of the tying medium, the second position of the tying medium intersecting the third position of the tying medium as a result of the first loop such that the third position is downstream of the second position in a direction of the first path, and is closer to the first retaining position than the second position is to the first retaining position in the first path;

a first moving portion configured to move the first loop relative to the second arm in synchronism with the switching operation of the switching mechanism from the first state to the second state to thus change a relative positional relationship between the first loop and the first position of the tying medium on the first path; and an operating part configured to operate the switching mechanism and the first moving portion, wherein the first position of the tying medium is alternately retained by the first retaining member and the second retaining member via a needle-like member having hardness and a sharp pointed shape.

26. The knot forming device according to claim 25, wherein the needle-like member has a first end having a sharp pointed shape and a second end having a sharp pointed shape, the first end being retained by the first retaining member in the first state, the second end being retained by the second retaining member in the second state.

27. The knot forming device according to claim 25, further comprising a locking member configured to lock the needle-like member with respect to one of the first retaining member and the second retaining member, wherein the needle-like member has a first end formed with a groove and a second end formed with a groove, the first end being retained by the first retaining member through the locking member in the first state, the second end being retained by the second retaining member through the locking member in the second state.

28. The knot forming device according to claim 25, wherein the first moving portion moves the tying medium in a direction separating from the base part in the first path.

29. A knot forming device configured to form a knot in a tying medium, the knot forming device comprising:
- a base part extending in a predetermined direction;
- a first arm disposed on the base part and having a first retaining member configured to detachably retain a first position of the tying medium at a first retaining position;
- a second arm disposed on the base part and having a second retaining member configured to detachably retain the first position of the tying medium at a second retaining position instead of the first retaining member;
- a switching mechanism configured to switch a retained state of the first position of the tying medium between a first state where the first position is retained by the first retaining member at the first retaining position and a second state where the first position is retained by the second retaining member at the second retaining position;
- a first loop forming member configured to form a first loop around the second arm in a first path of the tying medium, the first path extending from the first retaining position through a second position and a third position to a fourth position of the tying medium, the second position of the tying medium intersecting the third position of the tying medium as a result of the first loop such that the third position is downstream of the second position in a direction of the first path, and is closer to the first retaining position than the second position is to the first retaining position in the first path;
- the second arm functioning as a first loop retaining member configured to retain the first loop;
- a first moving portion configured to move the first loop relative to the second arm in synchronism with the switching operation of the switching mechanism from the first state to the second state to thus change a relative positional relationship between the first loop and the first position of the tying medium on the first path; and
- an operating part configured to operate the switching mechanism and the first moving portion,
- wherein the first loop retaining member retains the first loop by wrapping the tying medium around a portion between the base part and the second retaining member of the second arm in the first path, and
- wherein the first loop forming member comprises
  - a first rotating member configured to rotate the first arm and the second arm relative to a seventh position of the tying medium so as to wrap the tying medium around an axis extending in the predetermined direction, the seventh position being one end farther than the fourth position from the first position of the tying medium, and
  - a second rotating member configured to rotate the second arm N-number turns about an axis extending in a direction connecting the first retaining member and the second retaining member, where N is an integer.

30. The knot forming device according to claim 29, wherein the first arm and the second arm remain stationary relative to the base part while the base part rotates about an axis extending in the predetermined direction, and
- wherein the first rotating member rotates about the base part.

31. The knot forming device according to claim 29, wherein the first arm and the second arm remain stationary relative to the base part while the base part rotates about an axis extending in the predetermined direction, and
- wherein the first rotating member rotates about the base part while the base part rotates about the axis.

32. A knot forming device configured to form a knot in a tying medium, the knot forming device comprising:
- a base part extending in a predetermined direction;
- a first arm disposed on the base part and having a first retaining member configured to detachably retain a first position of the tying medium at a first retaining position;
- a second arm disposed on the base part and having a second retaining member configured to detachably retain the first position of the tying medium at a second retaining position instead of the first retaining member;
- a switching mechanism configured to switch a retained state of the first position of the tying medium between a first state where the first position is retained by the first retaining member at the first retaining position and a second state where the first position is retained by the second retaining member at the second retaining position;
- a first loop forming member configured to form a first loop around the second arm in a first path of the tying medium, the first path extending from the first retaining position through a second position and a third position to a fourth position of the tying medium, the second position of the tying medium intersecting the third position of the tying medium as a result of the first loop such that the third position is downstream of the second position in a direction of the first path, and is closer to the first retaining position than the second position is to the first retaining position in the first path;
- the second arm functioning as a first loop retaining member configured to retain the first loop;
- a first moving portion configured to move the first loop relative to the second arm in synchronism with the switching operation of the switching mechanism from the first state to the second state to thus change a relative positional relationship between the first loop and the first position of the tying medium on the first path;
- an operating part configured to operate the switching mechanism and the first moving portion;
- a second loop forming member configured to form a second loop around the first arm in a second path of the tying medium, the second path extending from the second retaining position through a fifth position and a sixth position to the fourth position of the tying medium, the fifth position of the tying medium intersecting the sixth position of the tying medium as a result of the second loop such that the sixth position is downstream of the fifth position in a direction of the second path, and is closer to the second retaining position than the fifth position to the second retaining position in the second path;
- the first arm functions as a second loop retaining member configured to retain the second loop; and
- a second moving portion configured to move the second loop relative to the first arm in synchronism with the switching operation of the switching mechanism from the second state to the first state to thus change a relative positional relationship between the second loop and the first position of the tying medium on the second path,
- wherein the operating part is further configured to operate the second moving portion.

33. The knot forming device according to claim 32, wherein the second loop retaining member retains the second loop by wrapping the tying medium around a portion between the base part and the first retaining member of the first retaining member of the first arm in the first path, and
wherein the second loop forming member comprises
a first rotating member configured to rotate the first arm and the second arm relative to a seventh position of the tying medium so as to wrap the tying medium around an axis extending in the predetermined direction, the seventh position being one end farther than the fourth position from the first position of the tying medium, and
a second rotating member configured to rotate the first arm N-number turns about an axis extending in a direction connecting the first retaining position and the second retaining position, where N is an integer.

34. The knot forming device according to claim 33, further comprising a guide member capable of moving the tying medium in a direction approaching the base part in the first path, and is configured to support an eighth position of the tying medium contacting the first arm, and
wherein the operating part operates the guide member such that a position of the guide member after the knot is formed is separated farther away from the base part than a position of the guide member while forming the knot.

\* \* \* \* \*